(12) United States Patent
Gannot et al.

(10) Patent No.: US 9,365,883 B2
(45) Date of Patent: Jun. 14, 2016

(54) SPECTROSCOPIC MEANS AND METHODS FOR IDENTIFYING MICROORGANISMS IN CULTURE

(71) Applicants: OPTICUL DIAGNOSTICS LTD., Hertzilia Pituach (IL); OPTICUL DIAGNOSTICS Inc., Rockville, MD (US)

(72) Inventors: Gallya Gannot, Rockville, MD (US); Dror Lederman, Qiryat Gat (IL); Hassan Moinuddin, Bristow, VA (US); Israel Gannot, Ramat Hasharon (IL)

(73) Assignees: OPTICUL DIAGNOSTICS LTD., Hertzilia Pituach (IL); OPTICUL DIAGNOSTICS INC., Rockville, MD (US)

( * ) Notice: Subject to any disclaimer, the term of this patent is extended or adjusted under 35 U.S.C. 154(b) by 63 days.

(21) Appl. No.: 14/367,060

(22) PCT Filed: Dec. 19, 2012

(86) PCT No.: PCT/IL2012/050534
§ 371 (c)(1),
(2) Date: Jun. 19, 2014

(87) PCT Pub. No.: WO2013/093913
PCT Pub. Date: Jun. 27, 2013

(65) Prior Publication Data
US 2014/0377795 A1    Dec. 25, 2014

Related U.S. Application Data

(60) Provisional application No. 61/577,131, filed on Dec. 19, 2011.

(51) Int. Cl.
*G01N 21/00* (2006.01)
*C12Q 1/04* (2006.01)
(Continued)

(52) U.S. Cl.
CPC ............. *C12Q 1/04* (2013.01); *G01N 21/255* (2013.01); *G01N 21/3577* (2013.01);
(Continued)

(58) Field of Classification Search
CPC ... H01J 37/32935; G01N 21/64; G01N 21/65; G01N 21/68; G01N 2015/1037; G01J 3/02
USPC ........................................................ 356/72–73
See application file for complete search history.

(56) References Cited

U.S. PATENT DOCUMENTS

| | | | |
|---|---|---|---|
| 4,683,202 A | 7/1987 | Mullis | |
| 4,847,198 A | 7/1989 | Nelson et al. | |

(Continued)

FOREIGN PATENT DOCUMENTS

| | | |
|---|---|---|
| WO | 90/04041 | 4/1990 |
| WO | 98/41842 | 9/1998 |

(Continued)

OTHER PUBLICATIONS

International Preliminary Examination Report dated Jun. 24, 2014 for PCT/IL12/50534.

(Continued)

*Primary Examiner* — Abdullahi Nur
(74) *Attorney, Agent, or Firm* — Paul D. Bianco; Fleit Gibbons Gutman Bongini & Bianco PL

(57) ABSTRACT

A spectroscopic method for spectroscopic detection and identification of bacteria in culture is disclosed. The method incorporates construction of at least one data set, which may be a spectrum, interference pattern, or scattering pattern, from a cultured sample suspected of containing said bacteria. The data set is corrected for the presence of water in the sample, spectral features are extracted using a principal components analysis, and the features are classified using a learning algorithm. In some embodiments of the invention, for example, to differentiate MRSA from MSSA, a multimodal analysis is performed in which identification of the bacteria is made based on a spectrum of the sample, an interference pattern used to determine cell wall thickness, and a scattering pattern used to determine cell wall roughness. An apparatus for performing the method is also disclosed, one embodiment of which incorporates a multiple sample analyzer.

19 Claims, 16 Drawing Sheets

(51) Int. Cl.
*G01N 21/65* (2006.01)
*G01N 21/3577* (2014.01)
*G01N 21/25* (2006.01)
*C12M 1/34* (2006.01)
*G01N 21/39* (2006.01)
*G01N 21/64* (2006.01)
*G01N 21/35* (2014.01)
*G01N 21/17* (2006.01)
*G06F 19/10* (2011.01)

(52) U.S. Cl.
CPC ............ *G01N 21/65* (2013.01); *G01N 21/658* (2013.01); *C12M 41/36* (2013.01); *G01N 21/39* (2013.01); *G01N 21/64* (2013.01); *G01N 2021/1742* (2013.01); *G01N 2021/1744* (2013.01); *G01N 2021/3595* (2013.01); *G01N 2021/6417* (2013.01); *G01N 2201/06113* (2013.01); *G01N 2201/129* (2013.01); *G01N 2201/1296* (2013.01); *G06F 19/10* (2013.01)

(56) References Cited

U.S. PATENT DOCUMENTS

| | | | |
|---|---|---|---|
| 5,447,836 | A | 9/1995 | Wolber et al. |
| 6,075,594 | A | 6/2000 | Thomas et al. |
| 6,379,920 | B1 | 4/2002 | El-Sayed et al. |
| 6,844,199 | B1 | 1/2005 | Nelson et al. |
| 2003/0097059 | A1 | 5/2003 | Sorrell et al. |
| 2004/0254474 | A1 | 12/2004 | Seibel et al. |
| 2005/0042606 | A9 | 2/2005 | Bergeron et al. |
| 2010/0049055 | A1* | 2/2010 | Freudenberg ........ A61B 5/0059 600/475 |
| 2010/0051788 | A1* | 3/2010 | Klunder ............. G01N 21/6452 250/216 |
| 2010/0136609 | A1 | 6/2010 | Clay et al. |
| 2010/0291618 | A1 | 11/2010 | Robinson et al. |
| 2011/0007309 | A1 | 1/2011 | Stewart et al. |
| 2011/0143332 | A1 | 6/2011 | Lin et al. |
| 2011/0178721 | A1 | 7/2011 | Ben-David et al. |
| 2011/0184654 | A1 | 7/2011 | Ben-David et al. |
| 2011/0294202 | A1 | 12/2011 | Wikswo et al. |
| 2012/0002199 | A1 | 1/2012 | Ben-David et al. |
| 2012/0211650 | A1 | 8/2012 | Jones et al. |

FOREIGN PATENT DOCUMENTS

| | | |
|---|---|---|
| WO | 2010041251 | 4/2010 |
| WO | 2010076801 | 7/2010 |
| WO | 2011063086 | 5/2011 |

OTHER PUBLICATIONS

International Search Report dated May 22, 2013 for International Application No. PCT/IL2012/050534.

Written Opinion mailed May 22, 2013 for International Application No. PCT/IL2012/050534.

Naumann et al. (Encyclopedia of Analytical Chemistry, R.A. Meyers (Ed.) pp. 102-131, John Wiley & Sons Ltd, Chichester, 2000).

Goff et al., "The Solution to the Cytological Paradox of Isomorphy". The Journal of Cell Biology, vol. 104, 1987, published Mar. 1, 1987; pp. 739-748.

Wilkinson et al., Cell Wall Composition and Associated Properties of Methicillin-Resistant *Staphylococcus aureus* Strains. Journal of Bacteriology, vol. 136, No. 3, Dec. 1978, p. 976-982.

* cited by examiner

SPECTROSCOPIC MEANS AND METHODS FOR IDENTIFYING MICROORGANISMS IN CULTURE

REFERENCE TO RELATED APPLICATIONS

This application claims priority from U.S. Provisional Patent Application No. 61/577,131, filed 19 Dec. 2011, which is hereby incorporated by reference in its entirety.

FIELD OF THE INVENTION

This invention is drawn to spectroscopic means and methods for identifying microorganisms in culture. In particular, it is drawn to means and methods for identifying microorganisms in culture that rely on spectroscopic measurements of the whole cell rather than of specific chemical constituents of the cell, as well as to means and methods that incorporate other light-based measurement methods such as interferometry.

BACKGROUND OF THE INVENTION

The identification of microorganisms, especially detection of antibiotic resistant bacteria, is of great importance in the medical field. It is well known that health care facilities invest large efforts to prevent patients from being infected with secondary diseases caused by environmental bacteria and especially those due to antibiotic resistant bacteria.

The commonly used method to distinguish between antibiotic resistant bacteria and antibiotic sensitive bacteria is to use PCR directly on a sample or after culturing the sample. Such a method is disclosed, for example, in U.S. Pat. No. 4,683,202. Another method is by detecting the proteome, i.e., different proteins expressed by a genome.

DNA-based methods for universal bacterial detection by detection of common bacterial pathogens are also known in the art, for example, as disclosed in U.S. Pat. Appl. Pub. No. 2005/0042606. Detection of viable bacteria in biological samples by exposing bacterial cultures obtained from the samples to transducing particles having a known host range has been disclosed in PCT Pub. No. WO90/04041.

A problem with these methods is that they generally take a significant amount of time (typically at least an hour) to produce a result, and can only be performed by a qualified professional technician. One possible approach to solving these problems might be the use of spectroscopic techniques, which are inherently faster than these methods. Some spectroscopic methods for identifying bacteria, not specific to antibiotic resistant strains, are already known in the art.

For example, PCT Pub. No. WO98/41842 discloses a system for the detection of bacteria antibody complexes by Raman spectroscopy. The sample to be tested for the presence of bacteria is placed in a medium which contains antibodies attached to a surface for binding to specific bacteria to form an antigen—antibody complex. Similarly, Resonance Raman backscattering is disclosed as a method for identification of a bacterium in U.S. Pat. No. 4,847,198. In these methods, the presence in the Raman spectrum of markers associated with particular bacteria is taken as an indication of the presence of the bacterium.

U.S. Pat. No. 6,379,920 discloses a spectroscopic method for detecting and identifying specific bacteria in a biologic sample, for which it is claimed that culturing is not required. The method includes obtaining spectra of a biological sample from a non-infected patient for use as a reference, subtracting the reference from the spectra of a possibly infected sample, and comparing the fingerprint regions of the resulting difference spectrum with reference spectra of known bacteria.

Naumann et al. (Encyclopedia of Analytical Chemistry, R. A. Meyers (Ed.) pp. 102-131, John Wiley & Sons Ltd, Chichester, 2000) have reported the use of FTIR spectroscopy for detection and classification of bacteria in dried samples. Live microbes have been identified by using FTIR and near-infrared FT-Raman spectroscopies. Other methods involve the use of fluorescence spectroscopy or a combination of the above spectroscopic techniques.

None of the prior art literature discloses means and methods that can quickly (less than one hour) and without the need for a professional technician detect and distinguish antibiotic resistant bacteria and antibiotic sensitive bacteria. Furthermore, none of the prior art literature discloses means and method that can eliminate the interference of water contained in a sample on the experimental signal in order to provide more sensitive and accurate detection of bacteria in general and antibiotic resistant bacteria in particular.

Thus, there is a long felt need for means and methods for rapid, sensitive, and accurate detection and identification of microorganisms from a primary culture plate sample without the use of additional reagents or complicated sample preparation, in particular, means and methods that can differentiate antibiotic-sensitive bacteria from antibiotic-resistant bacteria.

SUMMARY OF THE INVENTION

The invention herein disclosed is designed to meet this long-felt need. The invention discloses methods and systems for spectroscopic identification of microorganisms in culture. In particular, the method herein disclosed includes steps of removing artifacts in the spectrum due to water, uses Principal Components Analysis to extract spectral features of interest, and uses a learning algorithm such as the RANDOM FOREST classifier method to classify the spectral signatures. The method also incorporates steps for distinguishing antibiotic-resistant bacteria, for example, methicillin-resistant *Streptococcus aureus* (MRSA), from antibiotic-sensitive bacteria, for example, methicillin-sensitive *Streptococcus aureus* (MSSA), by using a multimodal technique that combines spectroscopy to determine at least one chemical characteristic of bacteria within a sample suspuses interferometry to determine the thickness of the bacterial cell wall.

It is therefore an object of the present invention to disclose a method for spectroscopic detection and identification of microorganisms in culture, wherein said method comprises:
1. Obtaining at least one cultured sample suspected of containing said microorganisms; transferring said cultured sample to a sample cell; interacting said sample with light obtained from a light source; measuring at least a portion of said light remaining after said step of interacting; constructing at least one data set from said measured light, wherein said data set comprises at least one type of data set selected from the group consisting of absorption spectrum, reflectance spectrum, fluorescence spectrum, scattering pattern, and interference pattern;
2. If said data set is a spectrum: preprocessing said data set by performing at least one step selected from the group consisting of (a) correcting said data set for signals due to the presence of water in said cultured sample, (b) removing a baseline, (c) reducing noise, and (d) extracting a spectral region of interest, thereby producing a corrected data set; extracting spectral features of interest from said corrected data set by using a principal component analysis (PCA) method and assigning the largest eigenvalues or components obtained from said principal component analysis as features, thereby producing a set of extracted spectral features, and classifying said extracted spectral features by using a method that incorporates a learning algorithm, thereby determining whether or not said microorganisms are present in said cultured sample;

3. If said data set is an interference pattern: estimating a cell wall thickness of said microorganisms from said interference pattern; and classifying said cell wall thickness, thereby determining whether or not said microorganisms are present in said cultured sample;

4. If said data set is a scattering pattern: estimating a cell wall roughness of said microorganisms from said scattering pattern; and classifying said cell wall roughness, thereby determining whether or not said microorganisms are present in said cultured sample.

It is a further object of this invention to disclose such a method, wherein said step of obtaining a cultured sample comprises: obtaining a biological sample; culturing said biological sample, thereby producing a cultured sample; and smearing said colonies on a surface. In some preferred embodiments of the invention, the step of culturing is followed by a step of selecting a plurality of colonies. In some preferred embodiments of the invention, said biological sample is in a form selected from the group consisting of solid form and liquid form. In some preferred embodiments of the invention, said biological sample is selected from the group consisting of sneeze, saliva, mucus, bile, urine, vaginal secretions, middle ear aspirate, pus, pleural effusions, synovial fluid, abscesses, cavity swabs, serum, blood and spinal fluid. In some preferred embodiments of the invention, said step of culturing said biological sample comprises culturing said biological sample contained in the sample are cultured in an agar plate for 12 to 24 hours. In some preferred embodiments of the invention, said step of smearing comprises smearing on a surface to cover a 2.5 cm diameter area. In some preferred embodiments of the invention, said step of smearing comprises smearing on the reflective surface of a mirror. In some preferred embodiments of the invention, wherein said reflective surface is gold.

It is a further object of this invention to disclose the method as defined in any of the above, wherein said step of transferring said cultured sample to a sample cell comprises transferring said cultured sample to a multiple pass cell.

It is a further object of this invention to disclose the method as defined in any of the above, wherein said step of obtaining at least one cultured sample comprises obtaining a plurality of cultured samples; said step of transferring said cultured sample to a sample cell comprises transferring each of said plurality of cultured samples to a sample cell disposed within a separate compartment of a multiple compartment analyzer; and said step of constructing a data set comprises constructing separately a data set for each of said plurality of samples.

In some preferred embodiments of the invention, each compartment of said multiple compartment analyzer comprises: an entrance aperture; an exit aperture aligned with said entrance aperture; a cell; and a switching device capable of directing light entering said compartment through said entrance aperture either to said cell or to said exit aperture without entering said cell. In some preferred embodiments of the invention, said switching device is a movable flip mirror movable between a first position in which light entering said compartment through said entrance aperture is reflected from said mirror into said cell and a second position in which light entering said compartment through said entrance aperture passes to said exit aperture without entering said cell. In other preferred embodiments of the invention, said switching device is an optical switch. In yet other preferred embodiments of the invention, said optical switch is fiber based.

In some preferred embodiments of the invention, said cell is a multiple pass cell. In some preferred embodiments of the invention that incorporate a multiple pass cell, said multiple pass cell comprises: a parabolic mirror; light converging means for converging output of said light source and disposed such that said output of said light source impinges on said parabolic mirror; light coupling means for directing light from multiple pass cell to a detector; a stage comprising sample holding means for holding a sample, said stage disposed such that at least a portion of light passing from said light source to said parabolic mirror via said light converging means and then reflected from said parabolic mirror will impinge upon a sample attached to said stage via said sample holding means and such that light reflected onto said parabolic mirror from said sample will be directed to a location other than said sample; and a plurality of n folding mirrors disposed such that light reflected from said sample to said parabolic mirror will impinge on one of said folding mirrors; for m=1 to n−1, light impinging on an mth folding mirror will be reflected back to said parabolic mirror such that it will then be reflected onto said sample, and such that light reflected from said sample will be reflected from said parabolic mirror to an (m+1)th folding mirror; and for m=n, light reflected from said mth folding mirror will be directed to said light coupling means. In some preferred embodiments of the invention, said plurality of n folding mirrors are disposed in pairs around the circumference of a circle. In some preferred embodiments of the invention, said plurality of n folding mirrors comprises seven pairs of mirrors.

It is a further object of this invention to disclose the method as defined in any of the above, wherein said light source comprises the light source of an FTIR spectrometer.

It is a further object of this invention to disclose the method as defined in any of the above, wherein said light source comprises the light source of a Raman spectrometer.

It is a further object of this invention to disclose the method as defined in any of the above, wherein said light source is a laser. In some preferred embodiments of the invention, said laser is selected from the group consisting of diode lasers, fiber lasers, and quantum cascade lasers.

It is a further object of this invention to disclose the method as defined in any of the above, wherein said step of constructing a data set comprises constructing a spectrum selected from the group consisting of infrared absorption spectrum, infrared reflectance spectrum, Raman spectrum, UV-VIS absorption spectrum, and UV-VIS reflectance spectrum. In some preferred embodiments of the invention, said step of constructing a data set comprises constructing an infrared absorption spectrum. In some preferred embodiments of the invention in which said step of constructing a data set comprises constructing an infrared spectrum, said step of preprocessing comprises extracting a spectral range selected from the group consisting of about 850-1000 $cm^{-1}$; about 990-1190 $cm^{-1}$; about 1180-1290 $cm^{-1}$; about 1235-1363 $cm^{-1}$; about 1300-1350 $cm^{-1}$; about 1500-1800 $cm^{-1}$; about 1550-1650 $cm^{-1}$; about 1720-1780 $cm^{-1}$; about 2800-3050 $cm^{-1}$; about 2836-2995 $cm^{-1}$; and about 3000-3300 $cm^{-1}$.

It is a further object of this invention to disclose the method as defined in any of the above, wherein said step of correcting said data set for the presence of data due to the presence of water in said cultured sample comprises a step chosen from the group consisting of (a) performing simple filtering by subtracting from said data set a data set constructed from an average of other data sets; (b) subtracting a reference data set from said data set; and (c) performing adaptive filtering by adaptive filtering using a reference signal to produce an optimal reduction in the contribution of the water signal to the as-measured sample spectrum.

It is a further object of this invention to disclose the method as defined in any of the above, wherein said step of preprocessing said data comprises reducing noise by using at least one technique selected from the group consisting of linear filtering, adaptive filtering, using a Savitzky-Golay filter, low pass filtering, and spectral subtraction.

It is a further object of this invention to disclose the method as defined in any of the above, wherein said step of using a PCA method comprises: obtaining first and second derivatives of said data set; and obtaining two coefficients for each derivative obtained.

It is a further object of this invention to disclose the method as defined in any of the above, wherein said set of extracted spectral features comprises spectral features selected from the group consisting of peak correlation, peak wavelength, peak height, peak width, peak cross section, peak area, at least one of the coefficients of a fitted polynomial curve, the total sum of areas under at least two peaks of the signal, linear predictive coding (LPC), mean value of the signal, variance value of the signal, skewness value, kurtosis value, Gaussian set of parameters ($\mu, \sigma, A_i$), peak intensity ratios, wavelet coefficients, and derivatives thereof.

It is a further object of this invention to disclose the method as defined in any of the above, wherein said learning algorithm is selected from the group consisting of Bayes classifier, support vector machine (SVM), linear discriminant functions, Fisher's linear discriminant, C4.5 algorithm tree, K-nearest neighbor, weighted K-nearest neighbor, Hierarchical clustering algorithm, a learning algorithm that incorporates an ensemble classifier that uses the methods developed by Breiman and Cutler, hidden Markov model, Gaussian mixture model (GMM), K-mean clustering algorithm, Ward's clustering algorithm, minimum least squares, and neural network algorithms. In some preferred embodiments of the invention, said learning algorithm incorporates an ensemble classifier that uses the methods developed by Breiman and Cutler.

It is a further object of this invention to disclose the method as defined in any of the above, wherein said step of classifying is performed based on parameters of a fit obtained by said learning algorithm based on features that have a minimum significance threshold. In some preferred embodiments of the invention, said minimum significance threshold is a 95% confidence limit. In some preferred embodiments of the invention, said minimum significance threshold is determined by a statistical test selected from the group consisting of $\chi^2$, Wilcoxon test, and Student's t-test.

It is a further object of this invention to disclose the method as defined in any of the above, wherein said microorganisms comprise bacteria selected from the group consisting of *Staphylococcus*; staph coagulase negative; *Staph. aureus, Streptococcus* spp.; *Streptococcus viridans* group; *Enterococcus* spp.; *Corynebacterium* spp., *Aerococcus* spp.; *Micrococcus* spp.; *Peptostreptococcus* spp.; *Lactococcus* spp.; *Leuconostoc* spp.; *Tothia* spp.; *Gemella* spp.; *Alcaligenes* spp.; *Alternaria* spp.; *Flavobacterium* spp.; *Bacillus* spp.; *Achromobacter* spp.; *Acinetobacter* spp.; *Acinobacillus* spp.; *Alcaligenes* spp.; *Campylobacter* spp.; *Edwardsiella* spp.; *Ehrlichia* spp.; *Enterobacter* spp.; *Ewingella* spp.; *Flavobateria*; *Hafnia* spp.; *Klebsiella* spp.; *Kluyvera* spp.; *Legionella* spp.; *Moraxella* spp.; *Morganella* spp.; *Neisseria* spp.; *Pasteurella* spp.; *Prevotella* spp.; *Proteus* spp.; *Providencia* spp; *Pseusomonas* spp.; *Rahnella* spp.; *Salmonella* spp.; *Serratia* spp.; *Shigella* spp.; *Sphingobacterium* spp.; *Vibrio* spp.; *Yershinia* spp.; *Neisseria* spp.; *Kingella* spp.; *Cardiobacterium*; non Tuberculosis mycobacteria (NTB), *Mycobacterium tuberculosis*; and *Mycobacterium avium*.

It is a further object of this invention to disclose the method as defined in any of the above, wherein said microorganisms comprise bacteria selected from the group consisting of *Staph. aureus; Staph. epidermidis; Staph. haemolyticus; Staph. lugdunensis; Staph. intermedius; Staph. hominis; Staph. simulans; Staph. warneri; Staph. saccharolyticus; Staph. Capitis;* all other coag. Neg. *Staphylococcus; Strep. pyogenes* Gr A; *Str. agalactiae* gr B; *Strep; Streptococcus* gr G; *Streptococcus* gr C; *Streptococcus* gr F; *Streptococcus* gr B; *Streptococcus* gr D; *Strep. constellatus; Strep. intermedius; Strep. acidominimus; Strep. bovis; Strep. anginosus; Strep. mutans; Strep. salivarius; Strep. sanguis; Strep. thermophilus; Strep. mitis; Strep. equi/equisim; Strep viridans; Enteroccocus faecalis; Enter. faecium; Enter. casseliflavus; Enter. gallinarum; Enter. avium; Enter. durans; List. monocytogenes; Corynebacterium diphtheriae; Micrococcus luteus; Micrococcus roseus; Aerococcus viridans; Bacillus Cereus; Acinetobacter haemolyticus; Acinetobact. baumanni; Acinetobact. junii; Acinetobacter lwoffi; Aeromonas hydrophila; Aeromonas sobria; Aeromonas veronii; Bacter. thetaiotaomicron; Bacter. distasonis; Bacter. stercoris; Bacter. uniformis; Bacteroides fragilis; Bacteroides ovatus; Bacteroides vulgatus; Burkholderia cepacia; Campylobacter coli; Campylobacter jejuni; Citrobacter amalonaticus; Citrobacter braakii; Citrobacter diversus; Citrobacter farmeri; Citrobacter freundii; Citrobacter koseri; Citrobacter sedlakii; Citrobacter youngae; Clistridum botulinum; Clostridum difficile; Clostridum perfringens; Clostridum sordellii; Clostridium tetani; E. coli; Enterobact. cancerogenus; Enterob. agglomerans; Enterob. gergoviae; Enterob. intermedium; Enterob. sakazakii; Enterobact. aerogenes; Enterobacter. cloacae; Escherichia hermanni; Kl. ornithinolytica; Kl. planticola; Kleb. pneumoniae; Klebsiella oxytoca; Klebsiella ozaenae; L. pneumophila; Morax. catarrhalis; Morganella morganii; Prev. melaninogenica; Prevotella bivia; Prevotella disiens; Prevotella oralis; Proteus mirabilis; Proteus penneri; Proteus vulgaris; Provi. rustigianii; Providencia rettgeri; Providencia stuartii; Pseud. aeruginosa; Pseud. alcaligenes; Pseud. fluorescens; Pseud. mendocina; Pseud. testosteroni; Pseudomonas diminuta; Pseudomonas putida; Pseudomonas stutzeri; Salm. paratyphi A; Salm. paratyphi B; Salmonella enterica; Salmonella group B; Salmonella group C; Salmonella group C1; Salmonella group C2; Salmonella group D; Salmonella typhi; Serr. liquefaciens; Serratia ficaria; Serratia fonticola; Serratia marcescens; Serratia odorifera; Serratia odorifera 1; Serratia plymuthica; Serratia rubidaea; Shigella boydii 1; Shigella flexneri; Shigella sonnei; Stenotr. maltophilia; Vibrio Parahaemolyticus; Vibrio Vulnificus; Yersinia enterocoliticus; Yersinia pseudotuberculosis; Neisseria meningitidis; Neisseria gonorrhoeae; N. sicca; N. subflava; Neisseria elongata; Eikenella corrodens; Branhamella catarrhalis; Bordetella pertussis; Haemophilus influenzae; Haemophilus parainfluenzae; Kingella spp.; Cardiobacterium spp.; Chromobacterium violaceum; M. tuberculosis; Mycobact. avium; Mycob. fortuitum; Mycob. simiae;* all other non TB Mycobacteria; NTM; *Actinomyces naeslundii; Actinomyces meyeri; Nocardia* spp.; *Brucella* spp.; *Cryptococcus neoformans;* and *Cryptococcus* spp. (non *neoformans*); *Streptococcus pneumonia* resistant to β lactamase and macrolides, *Streptococcus viridians* group resistant to β lactamase and aminoglycosides, *Enterococci* resistant to vancomycin and teicoplanin and highly resistant to penicillins and aminoglycosides, *Staphylococcus aureus* sensitive to and resistant to methicillin, other β-lactams, macrolides, lincosamides, and aminoglicozides, *Streptococcus pyogenes* resistant to macrolides, macrolide-resistant streptococci of groups B, C and G, Coagulase-negative staphylococci resistant to β lactams, aminoglycosides, macrolides, lincosamides and glycopeptides, multiresistant strains of *Listeria* and *corynebacterium, Peptostreptococcus* and *clostridium* (e.g. *C. Difficile*) resistant to penicillins and macrolides, *Haemophilus influenza* resistant to β lactamase, *Pseudomonas Aeruginosa, Stenotrophomonas maltophilia, Klebsiella pneumonia* resistant to antibiotics, and *Klebsiella Pneumonia* sensitive to antibiotics, aminoglycosides and macrolides.

It is a further object of this invention to disclose the method as defined in any of the above, wherein said microorganisms comprise microorganisms selected from the group consisting of yeast and fungi. In some preferred embodiments of the invention, said microorganisms are selected from the group consisting of *Candida* spp.; *Aspergillus* spp.; *Fusarium* spp.; and *Penicillium* spp. In some preferred embodiments of the invention, said microorganisms are selected from the group consisting of *Candida albicans; Candida glabrata; Candida krusei; Candida parapsilosis; Candida tropicalis; Aspergillus fumigatus; Aspergillus flavus; Aspergillus niger;* and *Aspergillus terreus*.

It is a further object of this invention to disclose the method as defined in any of the above, wherein said at least one data set comprises a spectrum, an interference pattern, and a scattering pattern. In some embodiments of the invention, said microorganisms are antibiotic-resistant and antibiotic-sensitive strains of a single species of bacteria; said spectrum is used to determine at least one chemical characteristic of bacteria within said sample; said interference pattern is used to estimate a cell wall thickness of bacteria within said sample; said scattering pattern is used to estimate a cell wall roughness of bacteria within said sample; and said step of classifying comprises classifying results of all of said spectrum, said interference pattern, and said scattering pattern. In some preferred embodiments of the invention, the antibiotic-resistant strain is methicillin-resistant *Staphylococcus aureus* and the antibiotic-sensitive strain is methicillin-sensitive *Staphylococcus aureus*.

It is a further object of this invention to disclose an apparatus for spectroscopic detection and identification of microorganisms in culture, wherein said apparatus comprises: a light source; a sample compartment comprising means for holding a sample cell containing a sample suspected of containing said microorganisms, said sample compartment in optical connection with said light source; a detector for measuring light following interaction between light emitted by said light source and said sample; control means in electronic connection with said light source and said detector for controlling collection of data; and analyzing means for performing preprocessing of said data, analysis of said data, and classification of said data.

It is a further object of this invention to disclose such an apparatus, wherein said sample compartment comprises a multiple pass cell.

It is a further object of this invention to disclose such an apparatus as defined in any of the above, wherein said sample compartment comprises a multiple compartment analyzer comprising a plurality of compartments. In some preferred embodiments of the invention, each compartment of said multiple compartment analyzer comprises an entrance aperture; an exit aperture aligned with said entrance aperture; a cell; and a movable flip mirror movable between a first position in which light entering said compartment through said entrance aperture is reflected from said mirror into said cell and a second position in which light entering said compartment through said entrance aperture passes to said exit aperture without entering said cell. In some preferred embodiments, said cell is a multiple pass cell.

In some preferred embodiments of the apparatus as defined above in which the apparatus comprises a multiple pass cell, said multiple pass cell comprises: a parabolic mirror; light converging means for converging output of said light source and disposed such that said output of said light source impinges on said parabolic mirror; light coupling means for directing light from multiple pass cell to a detector; a stage comprising sample holding means for holding a sample, said stage disposed such that at least a portion of light passing from said light source to said parabolic mirror via said light converging means and then reflected from said parabolic mirror will impinge upon a sample attached to said stage via said sample holding means and such that light reflected onto said parabolic mirror from said sample will be directed to a location other than said sample; and a plurality of n folding mirrors disposed such that light reflected from said sample to said parabolic mirror will impinge on one of said folding mirrors; for m=1 to n−1, light impinging on an mth folding mirror will be reflected back to said parabolic mirror such that it will then be reflected onto said sample, and such that light reflected from said sample will be reflected from said parabolic mirror to an (m+1)th folding mirror; and for m=n, light reflected from said mth folding mirror will be directed to said light coupling means. In some preferred embodiments of the invention, said plurality of n folding mirrors are disposed in pairs around the circumference of a circle. In some preferred embodiments of the invention, said plurality of n folding mirrors comprises seven pairs of mirrors.

It is a further object of this invention to disclose such an apparatus as defined in any of the above, wherein said light source emits light in a wavelength range selected from the group consisting of UV, visible, IR, near-IR, mid-IR, far-IR, microwave, and terahertz.

It is a further object of this invention to disclose such an apparatus as defined in any of the above, wherein said light source comprises the light source of an FTIR spectrometer.

It is a further object of this invention to disclose such an apparatus as defined in any of the above, wherein said light source comprises the light source of a Raman spectrometer.

It is a further object of this invention to disclose such an apparatus as defined in any of the above, wherein said light source is a laser. In some preferred embodiments of the invention, said laser is selected from the group consisting of diode lasers and quantum cascade lasers.

BRIEF DESCRIPTION OF THE DRAWINGS

The invention will now be described with reference to the drawings, wherein.

DETAILED DESCRIPTION OF THE PREFERRED EMBODIMENTS

Figure 1A:
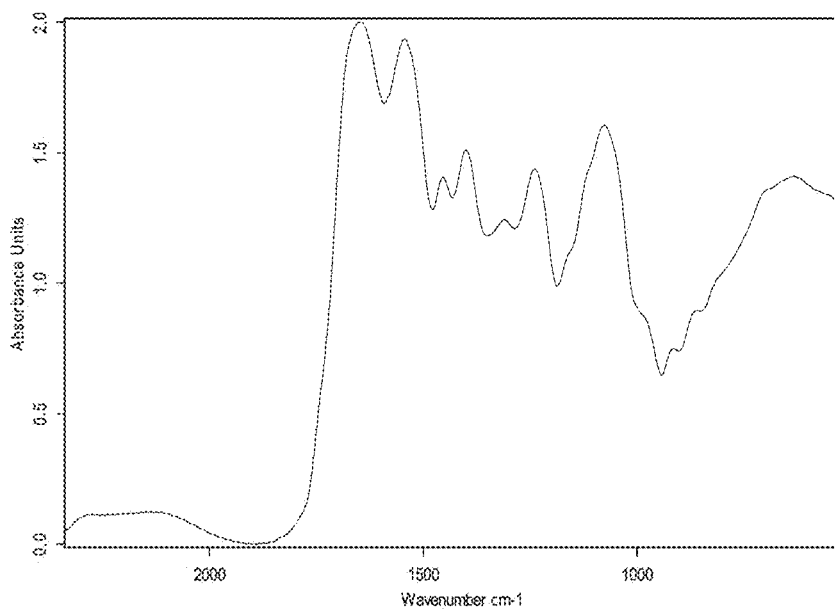
FIG. 1 presents spectra of a sample showing correction of a spectrum for signals due to the presence of water.

In the following description, various aspects of the invention will be described. For the purposes of explanation, specific details are set forth in order to provide a thorough understanding of the invention. It will be apparent to one skilled in the art that there are other embodiments of the invention that differ in details without affecting the essential nature thereof. Therefore the invention is not limited by that which is illustrated in the figure and described in the specification, but only as indicated in the accompanying claims, with the proper scope determined only by the broadest interpretation of said claims.

As used herein, the term "about" refers to a range of 25% above or below the nominal value.

As used herein, the term "RANDOM FORESTS" refers generically to a learning algorithm that incorporates an ensemble classifier that uses the methods developed by Breiman and Cutler, and specifically to the algorithm as implemented in the commercially available RANDOM FORESTS software package.

The method disclosed herein comprises steps of preparing a cultured sample that is suspected of containing at least one predetermined species of microorganism, transferring the sample to a sample cell, interacting the sample with light from a predetermined light source, constructing a data set such as a spectrum or interference pattern, and classifying the data set, thereby determining whether or not the microorganisms are present in the cultured sample. In the case in which the data set is a spectrum, the step of classifying the data set is preceded by preprocessing the data set, which in preferred embodiments includes at least one step of correcting the spectrum for the presence of water, removing a baseline, filtering, or extracting a spectral region of interest, and a step of extracting spectral features of interest by using a Principal Components Analysis (PCA) method. In preferred embodiments of the invention in which the data set is a spectrum, the classification is done by a learning algorithm. In more preferred embodiments, the learning algorithm is an ensemble classifier that uses a random subspace method and consists of many decision trees that outputs the class that is the mode of the classes output by individual decision trees. In the most preferred embodiments, commercially available software that implements the RANDOM FORESTS method is used.

While in preferred embodiments, infrared absorption spectroscopy is used to produce the data set, the method disclosed herein is general and may be used with any appropriate form of spectroscopy. Non-limiting examples of other spectroscopic methods that can be used with the method herein disclosed include infrared reflectance spectroscopy, Raman spectroscopy, fluorescence spectroscopy, UV-VIS absorption spectroscopy, and UV-VIS reflectance spectroscopy.

In one preferred embodiment of the method, the following sample preparation protocol is used. First, a biological sample is collected. The sample can be in either the solid or liquid form. Non-limiting examples of the kinds of biological samples that can be used with the method herein disclosed include sneeze, saliva, mucus, bile, urine, vaginal secretions, middle ear aspirate, pus, pleural effusions, synovial fluid, abscesses, cavity swabs, serum, blood and spinal fluid.

The microorganisms contained in the sample are cultured. In preferred embodiments of the invention, the sample is cultured on a petri dish. In the most preferred embodiments of the invention, the sample is cultured in a blood agar plate, typically for 12 to 24 hours. In embodiments in which analysis of a single species of microorganism is desired, after the culture, the microorganisms are checked for purity. In preferred embodiments of the invention, microorganisms are then transferred to a sample compartment by picking a plurality of colonies (typically, about four colonies are picked for every measurement performed) using a disposable cotton swab and smearing on the surface to cover a 1 inch diameter area. The sample is then transferred to a sample cell.

In preferred embodiments of the method, the sample is transferred to a sample compartment comprising a multiple pass cell. In more preferred embodiments of the invention, the sample is transferred to the multiple pass cell described in detail below. In embodiments in which this type of multiple pass cell is used, the sample is smeared on at the center of a mirror placed in the multiple pass cell. In the most preferred embodiments of the invention, the surface of the mirror is gold.

In some embodiments of the invention, multiple samples are analyzed simultaneously, and in preferred embodiments in which multiple sample analysis is performed, the sample is transferred to one compartment of a multiple sample analyzer. In preferred embodiments of the invention, the multiple sample analyzer is of the type described in detail below. In typical embodiments of the invention, multiple spectra are obtained and averaged; for example, using a commercially available spectrometer and control software, it is possible to obtain 64 absorption spectra within 1 second.

The sample is then irradiated from a light source. The light source can be any type of source known in the art that can produce the type of data set desired for analysis. In some embodiments of the invention, the light is used (after interaction with the sample) to create a spectrum. As a non-limiting example, if the data set is to be an infrared absorption or reflectance spectrum, any source of infrared light that spans the wavelength range desired can be used. The IR source can be a broadband source such as the light source of a commercially available IR spectrometer, or it can be a tunable narrow-band source such as a diode laser or quantum cascade laser (QCL). As another non-limiting example, if a Raman or fluorescence spectrum is to be obtained, a narrow-band source such as a laser or filtered lamp can be used. As a further non-limiting example, if a UV-VIS absorption or reflectance spectrum is to be measured, the light source can be any source of UV and visible light known in the art that is suitable for the measurement of a UV-VIS spectrum.

The light is then directed from the source to the sample and from the sample after one or more passes to a detector, where the light is measured and analyzed. The detector can be any appropriate type of detector known in the art. In some embodiments of the invention in which the irradiating light is obtained from the source of a commercially available FTIR or FT-Raman spectrometer, the detector used is the detector supplied with the spectrometer.

In preferred embodiments of the method disclosed herein in which the light measured by the spectrometer is used to construct a spectrum, the spectrum undergoes preprocessing prior to the analysis in order to produce a corrected spectrum.

Figure 1B:
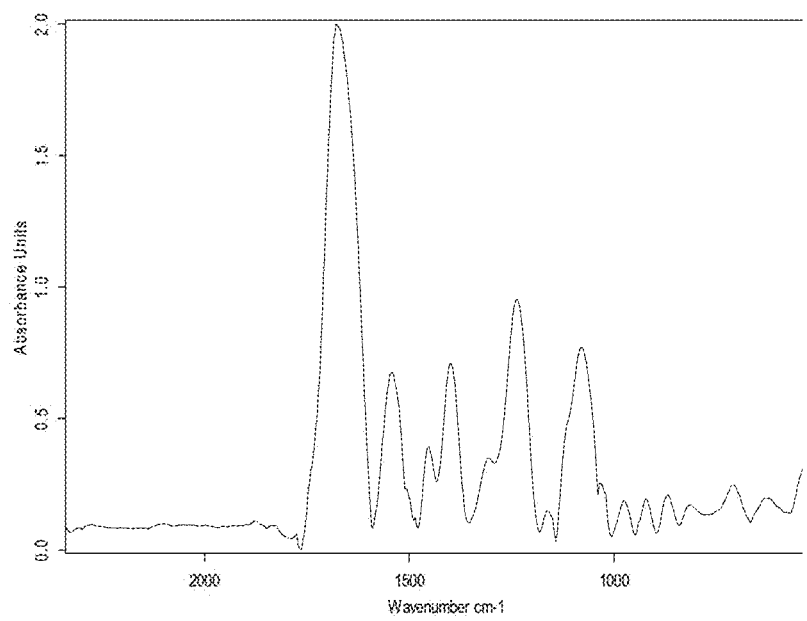

In preferred embodiments of the method, the preprocessing includes correcting the as-measured spectrum for signals due to the presence of water in the sample. In the most preferred embodiments of the invention, the correction for the presence of water is performed using at least one of three techniques. In some embodiments, spectral subtraction is performed in which a spectrum of water, normalized to the intensity of the as-measured spectrum, is subtracted from the as-measured spectrum. In other embodiments, a simple filter is used for each sample, in which for each sample, an average of the spectra of a plurality of other samples is created and subtracted. In yet other embodiments, the correction for signals due to the presence of water is performed by adaptive filtering using a reference signal to produce an optimal reduction in the contribution of the water signal to the as-measured sample spectrum. Algorithms for spectral subtraction, simple filtering, and adaptive filtering are well-known in the art, and any appropriate commercially available algorithm or software can be used. Reference is now made to FIG. 1, which shows an as-measured spectrum before correction for signals due to water (FIG. 1A), and the same spectrum after the correction is performed (FIG. 1B).

In preferred embodiments of the method, the preprocessing further includes performing baseline correction on the as-measured spectrum. Methods for performing baseline correction are well-known in the art, and any appropriate method known in the art may be used.

In preferred embodiments of the method disclosed in the present invention, the preprocessing further includes noise reduction. Numerous techniques for reducing the noise in a spectrum are known in the art. Non-limiting examples of such techniques contemplated by the inventors as being within the scope of the invention include linear filtering, adaptive filtering, using a Savitzky-Golay filter, low pass filtering, spectral subtraction, or any combination thereof.

Because the spectral information of interest is frequently only found within a limited portion of the spectrum, in preferred embodiments of the method disclosed in the invention, it includes a step of extracting a spectral region of interest. As non-limiting examples, in various embodiments in which the data set obtained from the sample is a vibrational spectrum, the spectral region of interest may be a spectral range selected from the group consisting of about 850-1000 cm$^{-1}$; about 990-1190 cm$^{-1}$; about 1180-1290 cm$^{-1}$; about 1235-1363 cm$^{-1}$; about 1300-1350 cm$^{-1}$; about 1500-1800 cm$^{-1}$; about 1550-1650 cm$^{-1}$; about 1720-1780 cm$^{-1}$; about 2800-3050 cm$^{-1}$; about 2836-2995 cm$^{-1}$; and about 3000-3300 cm$^{-1}$.

Figure 2A:
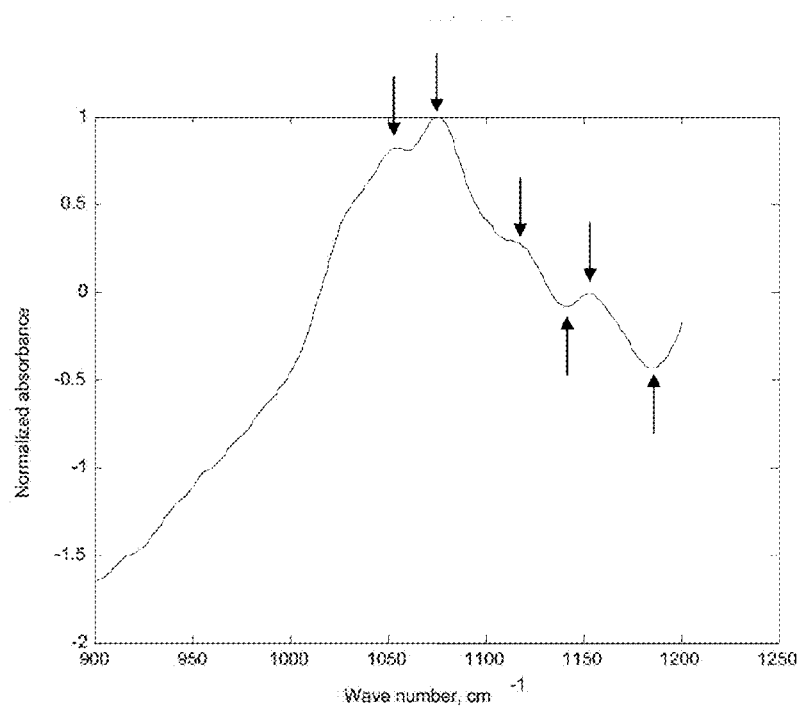
FIG. 2 presents examples of spectra indicating spectral features of interest as determined by principal components analysis.
Figure 2B:
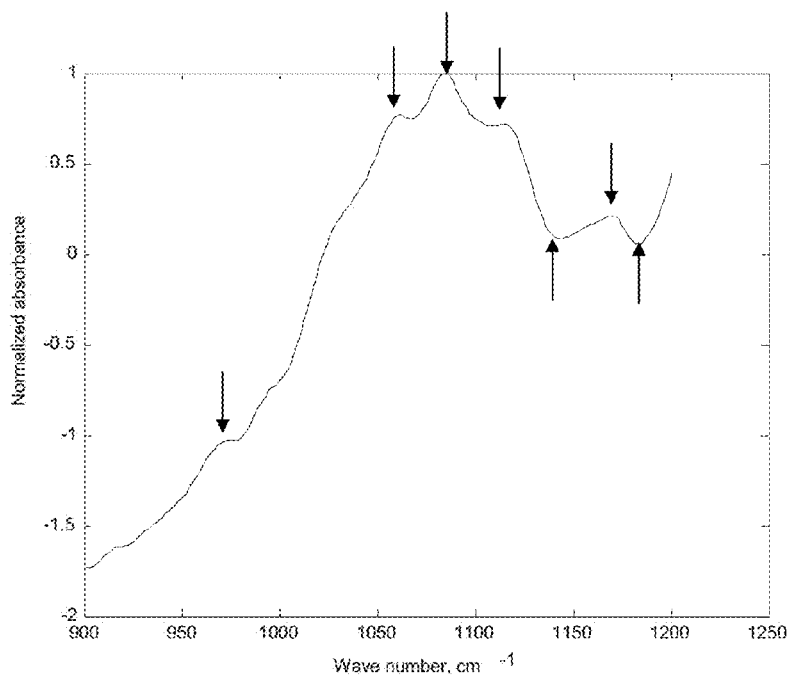

Following the preprocessing, spectral features of interest are extracted from the corrected data set (spectrum) by principal components analysis (PCA). Any principal components analysis method known in the art may be used. In preferred embodiments of the method disclosed in the present invention, the first and second derivatives of the spectrum are determined, from each of which at least two coefficients are determined, i.e. a total of at least four coefficients are obtained. Other analyses in which higher derivatives or larger or smaller numbers of coefficients are obtained are contemplated by the inventors as being within the scope of the invention. Reference is now made to FIG. 2, which presents two sample spectra with arrows indicating spectral features unique to the species of bacterium analyzed. These spectral features are non-limiting examples of spectral features that are extracted from the spectra by PCA. The figure presents two sample spectra, and the features extracted from the spectra indicated by arrows. Non-limiting examples of spectral features that can be extracted from the spectrum and used for the determination of the presence of a particular type of bacterium in the sample include peak correlation, peak wavelength, peak height, peak width, peak cross section, peak area, at least one of the coefficients of a fitted polynomial curve, the total sum of areas under at least two peaks of the signal, linear predictive coding (LPC), mean value of the signal, variance value of the signal, skewness value, kurtosis value, Gaussian set of parameters ($\mu, \sigma, A_i$), peak intensity ratios, wavelet coefficients, and derivatives thereof.

Once the preprocessing has been performed, the spectral features extracted are then classified, thereby determining whether or not the microorganisms of interest are present in the sample. In preferred embodiments of the invention, the classification is performed by using an algorithm chosen from the group consisting of supervised learning, machine learning, or pattern recognition algorithms. Many such algorithms are known in the art. Non-limiting examples of classification algorithms that can be used with the method disclosed herein include Bayes classifier, support vector machine (SVM), linear discriminant functions, Fisher's linear discriminant, C4.5 algorithm tree, K-nearest neighbor, weighted K-nearest neighbor, Hierarchical clustering algorithm, RANDOM FORESTS, hidden Markov model, Gaussian mixture model (GMM), K-mean clustering algorithm, Ward's clustering algorithm, minimum least squares, and neural network algorithms. In the most preferred embodiments of the invention, the RANDOM FORESTS algorithm is used. All of these learning algorithms begin with a training protocol to produce of a database of spectral features associated with known types of microorganisms. This database is then stored, and the classification of an unknown sample is then performed based on the results of the learning algorithm's comparison of the spectral features extracted from the sample with those of the spectral features obtained in the training procedure. In some embodiments of the invention, the parameters of the fit are chosen such that the classification is done based on features that have a predetermined minimum significance threshold. In some preferred embodiments of the invention, this minimum significance threshold is a 95% confidence limit. Non-limiting examples of statistical significance tests for determining whether a particular feature obtained by PCA passes the predetermined significance threshold include $\chi^2$, Wilcoxon test, and Student's t-test.

Figure 3A:
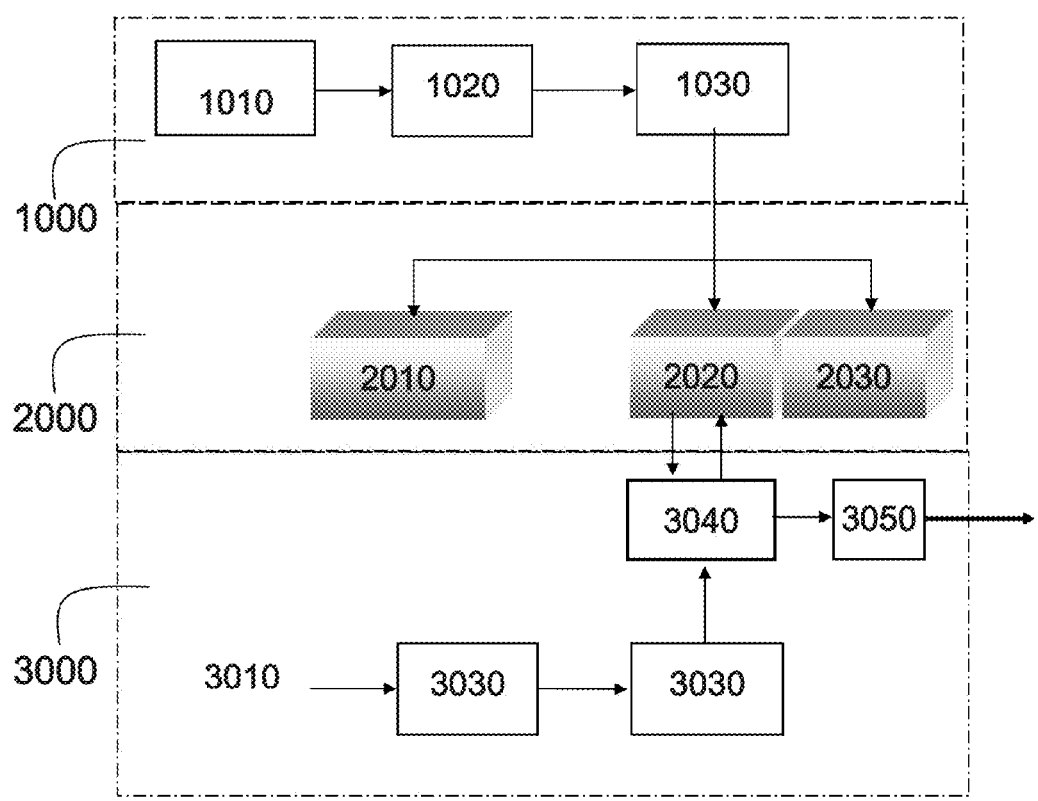
FIG. 3 presents flowcharts illustrating the steps of one preferred embodiment of the method herein disclosed.
Figure 3B:
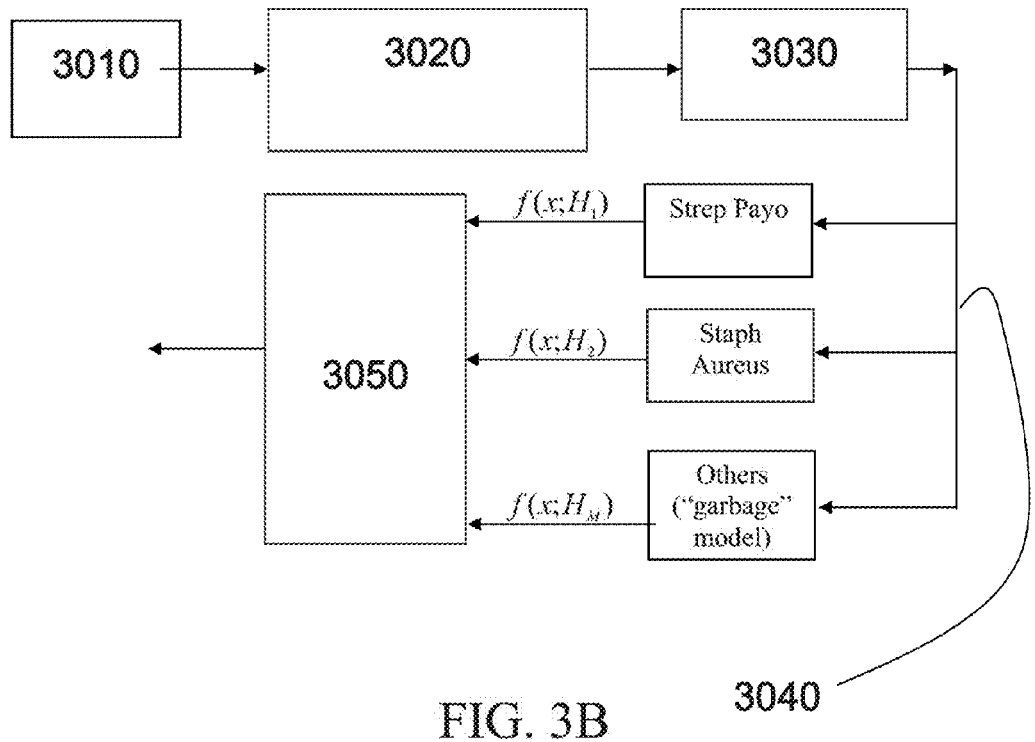

Reference is now made to FIG. 3, which presents a flowchart illustrating the steps in one preferred embodiment of the method herein disclosed. FIG. 3A illustrates in broad outline the steps of the method. As discussed above, the method is divided into three phases: training (1000), memory (2000), and testing (3000). The training phase involves obtaining at least one data set for a predetermined number of known types of microorganisms (1010), followed by preprocessing of the data sets (1020) to produce corrected data sets and feature extraction (1030). Once the training procedure has been completed, the extracted features are stored during the memory phase. The figure illustrates three non-limiting examples (2010, 2020, 2030) of bacterial types, the model spectra of which are used as the data base for the decision making process. The training and memory phases are not limited to any particular number of known microorganisms. In the testing phase, a sample suspected of containing one or more particular types of microorganism is used to produce a data set as described above (3010). The as-measured spectrum undergoes preprocessing (3020) and spectral features are extracted from the corrected spectrum (3030) as discussed above. The classification algorithm is then run (3040) with reference to the results obtained in memory phase 2000. Finally, a decision is made based on the results of the classification algorithm as to whether or not the suspect microorganism is present. FIG. 3B presents a more detailed flowchart of the steps of the testing phase for three non-limiting examples of bacteria suspected of being present in the sample.

Because the method involves the use of a learning algorithm, it can be used in a number of different situations. Non-limiting examples in which the method herein disclosed can be applied include: determination that a particular predetermined type of microorganism is or is not present in a cultured sample; determination that a particular predetermined type of microorganism is or is not present in a cultured sample in the presence of one or more other types of microorganisms; and determination that a sample contains microorganisms and identification of the type or types of microorganism present or confirmation that the microorganisms present do not match any of the types in the database.

Non-limiting examples of types of bacteria that can be detected and identified by the method disclosed herein include *Staphylococcus; staph* coagulase negative; *Staph. aureus, Streptococcus* spp.; *Streptococcus viridans* group; *Enterococcus* spp.; *Corynebacterium* spp., *Aerococcus* spp.; *Micrococcus* spp.; *Peptostreptococcus* spp.; *Lactococcus* spp.; *Leuconostoc* spp.; *Tothia* spp.; *Gemella* spp.; *Alcaligenes* spp.; *Alternaria* spp.; *Flavobacterium* spp.; *Bacillus* spp.; *Achromobacter* spp.; *Acinetobacter* spp.; *Acinobacillus* spp.; *Alcaligenes* spp.; *Campylobacter* spp.; *Edwardsiella* spp.; *Ehrlichia* spp.; *Enterobacter* spp.; *Ewingella* spp.; *Flavobateria; Hafnia* spp.; *Klebsiella* spp.; *Kluyvera* spp.; *Legionella* spp.; *Moraxella* spp.; *Morganella* spp.; *Neisseria* spp.; *Pasteurella* spp.; *Prevotella* spp.; *Proteus* spp.; *Providencia* spp; *Pseusomonas* spp.; *Rahnella* spp.; *Salmonella* spp.; *Serratia* spp.; *Shigella* spp.; *Sphingobacterium* spp.; *Vibrio* spp.; *Yershinia* spp.; *Neisseria* spp.; *Kingella* spp.; *Cardiobacterium;* non Tuberculosis mycobacteria (NTB), *Mycobacterium tuberculosis;* and *Mycobacterium avium.*

The method can also be used to detect and identify yeast and fungi. Non-limiting examples of types of yeast and fungi that can be detected and identified by the method disclosed herein include *Candida* spp.; *Aspergillus* spp.; *Fusarium* spp.; and *Penicillium* spp. Non-limiting examples of individual species of yeast and fungi that can be detected and identified by the method disclosed herein include *Candida albicans; Candida glabrata; Candida krusei; Candida parapsilosis; Candida tropicalis; Aspergillus fumigatus; Aspergillus flavus; Aspergillus niger;* and *Aspergillus terreus.*

In some embodiments of the method, instead of or in addition to a spectrum, an interference pattern or scattering pattern is measured. These embodiments are particularly useful for identification of bacteria by differences in their physical, rather than purely chemical, characteristics. As a non-limiting example, interference patterns generated from irradiation of a sample by monochromatic light can be used to estimate cell wall or cell membrane thickness, and scattering patterns can be used to estimate cell wall roughness, using analysis methods that are well-known in the art.

As a non-limiting example of an embodiment of the method disclosed in the present invention that incorporates construction and analysis of data sets other than spectra, it has been reported that the cell wall of methicillin-resistant *Staphylococcus aureus* (MRSA) is thicker than that of methicillin-sensitive *Staphylococcus aureus* (MSSA); see, for example, Kawai, M. et al., "Cell-Wall Thickness: Possible Mechanism of Acriflavine Resistance in Meticillin-Resistant *Staphylococcus Aureus,*" *J. Med. Microbiol.* 2009, 58(Pt 3), 331-336, which is hereby incorporated by reference in its entirety. It has also been reported that the roughness of the cell wall of MRSA differs from that of MSSA; see, for example, Wilkinson, B. J. et al., "Cell Wall Composition and Associated Properties of Methicillin-Resistant *Staphylococcus Aureus* Strains," *J. Bacteriol.* 1978, 136, 976-82, which is hereby incorporated by reference in its entirety. It is thus within the scope of the invention to provide a multi-modal method for distinguishing antibiotic-resistant from antibiotic-sensitive strains of a single species of bacteria. As a non-limiting example, the method can be used to distinguish MRSA from MSSA. In these embodiments, the step of constructing at least one data set comprises constructing a spectrum, an interference pattern, and a scattering pattern. The spectrum is analyzed as described in detail above to confirm the presence of the bacterium of interest (e.g. *Staphylococcus aureus*). An interference pattern is obtained by passing the light from the light source to the sample and light scattered by the sample through an interferometer (in preferred embodiments, a Mach-Zehnder interferometer is used), and from the interference pattern, determining the cell wall thickness of the bacteria in the sample. The measured cell wall thickness is then compared with the known thicknesses of the cell walls of the antibiotic-resistant and antibiotic-sensitive bacteria (e.g. MRSA and MSSA) and the bacteria in the sample are classified as being antibiotic-resistant or antibiotic-sensitive (e.g. MRSA or MSSA) according to the measured cell wall thickness. In preferred embodiments of the invention, the method additionally comprises measuring the spatial distribution of light of a predetermined wavelength scattered from the bacterial cells in the sample. From the scattering plot, the roughness of the bacterial cell wall is estimated using analytical methods known in the art, and the measured roughness compared with the known roughnesses of the cell walls of the antibiotic-resistant and antibiotic-sensitive bacteria (e.g. MRSA and MSSA), and the bacteria in the sample classified accordingly.

Figure 4:
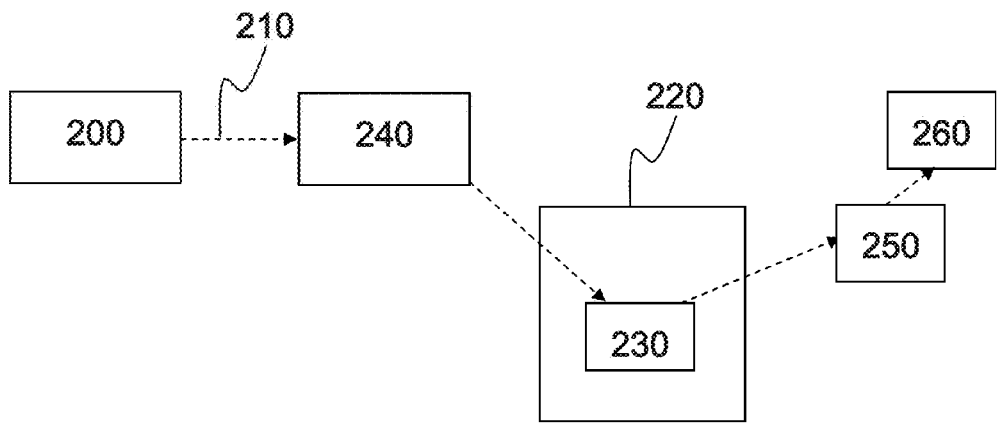
FIG. 4 presents a schematic block diagram of an apparatus for performing the method disclosed herein.

It is also within the scope of the invention to disclose an apparatus for making the measurements used in the method disclosed in the present invention. Reference is now made to FIG. 4, which presents a schematic illustration of the main components of such an apparatus 20. The apparatus comprises a light source 200; a sample compartment 220 for holding a sample 230; means 240 for passing light 210 from the source to the sample 230; a detector for measuring light scattered and/or transmitted by the sample following irradiation of the sample by light from the source 250; and means for passing light from the sample compartment to the detector 260.

Light source 200 can be any light source known in the art appropriate for producing a desired data set type (spectrum, interference pattern, scattering pattern, etc.). In various embodiments of the invention, the light source emits light in a frequency range selected from the group consisting of UV, visible, IR, near-IR, mid-IR, far-IR, microwave, and terahertz. Depending on the type of data set desired, the light source may be broadband or monochromatic, and if monochromatic, fixed frequency or tunable. In some embodiments of the invention in which the data set is an IR spectrum, the light source is a standard broadband IR light source such as those found in commercially available IR spectrometers (e.g. globar or Nernst glower). In some other embodiments in which the data set is a spectrum, the light source is a tunable laser. Non-limiting examples of tunable lasers appropriate for use with the apparatus herein disclosed include tunable diode lasers and quantum cascade lasers. In embodiments in which interferometry is used, the light source can be any essentially monochromatic light source known in the art for such measurements (e.g. a lamp coupled with a filter or monochromator, a laser, etc.).

Figure 5:
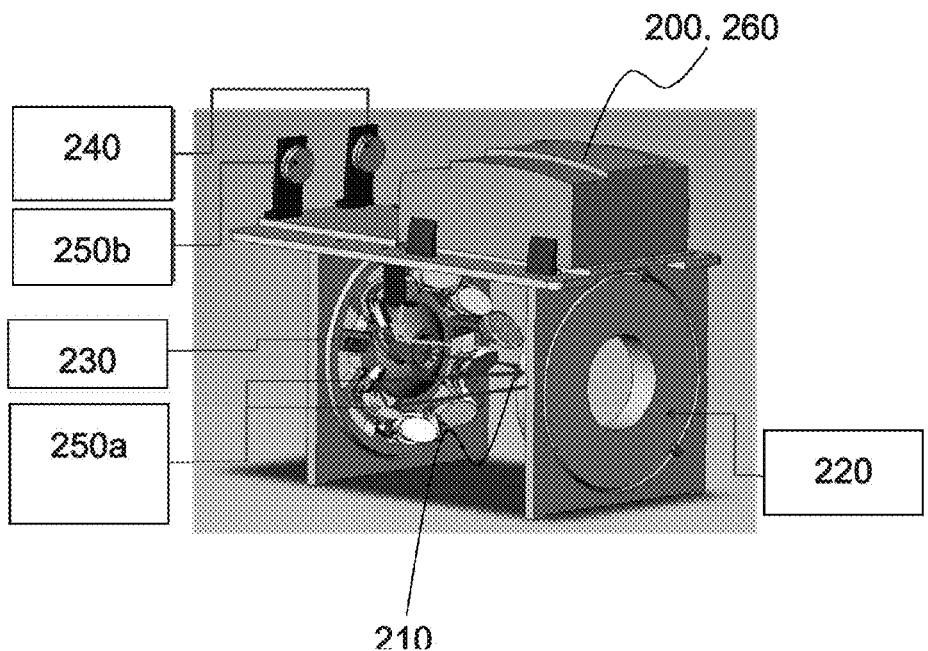
FIG. 5 presents a schematic illustration of one embodiment of an apparatus for performing the method disclosed herein.

Reference is now made to FIG. 5, which schematically illustrates the apparatus according to one embodiment of the invention. In this embodiment, in which the data set is an IR spectrum, light source 200 and detector 260 of a commercially available FTIR spectrometer are used. Light 210 from the source exits the FTIR spectrometer, impinging on spherical mirror 240 that focuses the light and directs it to external sample compartment 220. In the embodiment shown, sample compartment 220 is a multiple-pass cell of the type disclosed in U.S. Pat. Appl. Pub. No. 20120002199, which is hereby incorporated by reference in its entirety. In the particular embodiment shown, the external sample compartment is a multiple-pass cell that provides a plurality of interactions with sample 230. The light is directed to the detector by a series of mirrors 250a disposed within the sample chamber, which direct the light to the sample, and after multiple passes, external to the sample compartment to a spherical mirror 250b that focuses the light on detector 260. In the embodiment shown, the detector provided with the FTIR spectrometer is used, but any detector suitable for providing the desired data set can be used, and disposed in any location that is convenient for the operator of the apparatus.

Figure 6:
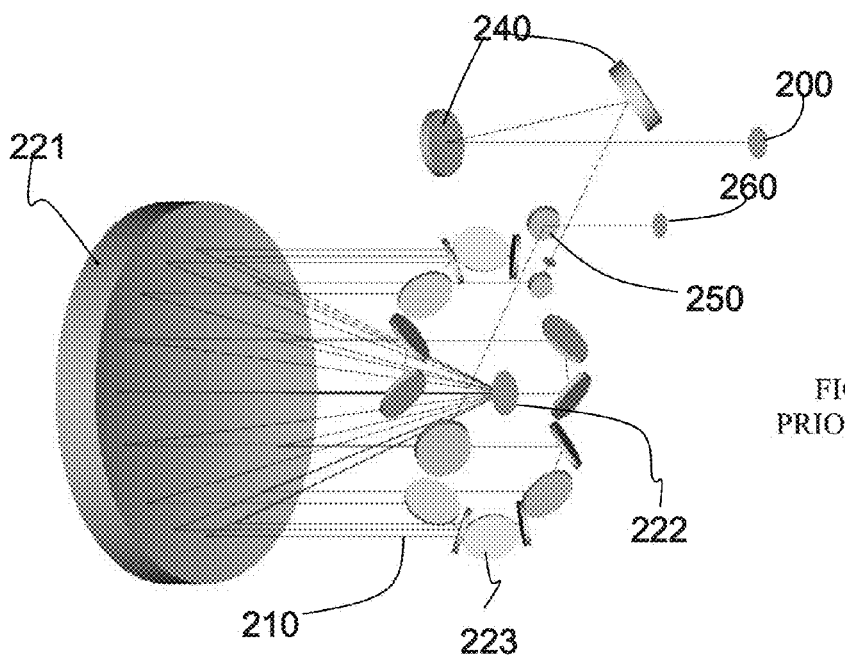
FIG. 6 presents a detailed illustration of the path of light through a multiple-pass sample compartment, of a type known in the art, used in the apparatus disclosed herein.

The multiple-pass cell 220 shown in FIG. 5 comprises a parabolic mirror 221; a stage 222 comprising sample holding means for holding sample 230, said stage disposed such that at least a portion of light passing from said light source to said parabolic mirror via said light converging means and then reflected from said parabolic mirror will impinge upon a sample attached to said stage via said sample holding means and such that light reflected onto said parabolic mirror from said sample will be directed to a location other than said sample; and a plurality of n folding mirrors 223 disposed such that light reflected from said sample to said parabolic mirror will impinge on one of said folding mirrors; for m=1 to n−1, light impinging on an mth folding mirror will be reflected back to said parabolic mirror such that it will then be reflected onto said sample, and such that light reflected from said sample will be reflected from said parabolic mirror to an (m+1)th folding mirror; and for m=n, light reflected from said mth folding mirror will be directed to said light coupling means. In preferred embodiments of the invention, n=14 (i.e. there are seven pairs of folding mirrors). Reference is now made to FIG. 6, which shows in greater detail the arrangement of the mirrors that bring the light from source 200 through the multiple-pass cell to detector 260.

Figure 7A:
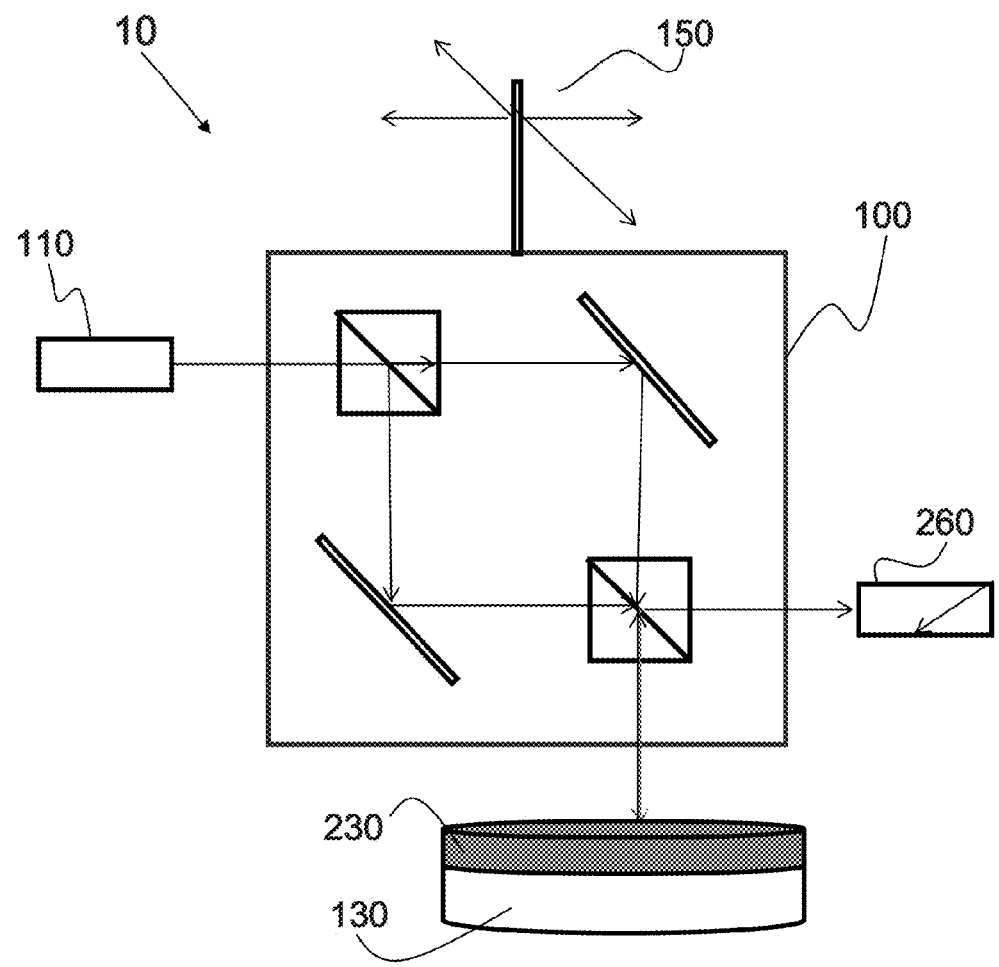
FIG. 7 presents a schematic illustration of an interferometry setup according to one embodiment of the invention.
Figure 7B:
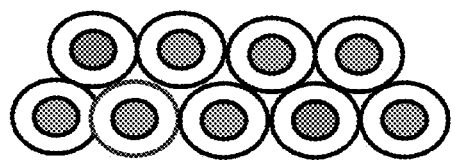
Figure 7C:
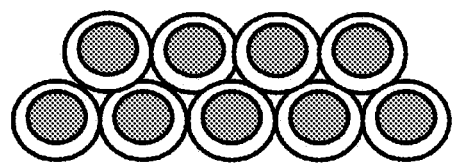

Reference is now made to FIG. 7A, which illustrates a typical embodiment 10 of a setup for performing an interference measurement. A Mach-Zehnder interferometer 100 is used. Light from source 200 (in preferred embodiments, the light is from an essentially monochromatic source such as a laser; in some preferred embodiments, a visible or NIR diode laser is used) passes through the interferometer onto sample 230, which sits on a mirror 130. The reflected light is then passed back into the interferometer and onto the element of detector 260. The sample is scanned by x-y scanner 150. The interference pattern thus obtained will depend on the thickness of the cell wall and will be different for a sample containing bacteria with thicker cell walls (FIG. 7B) than for a sample containing bacteria with thinner cell walls (FIG. 7C).

Figure 8:
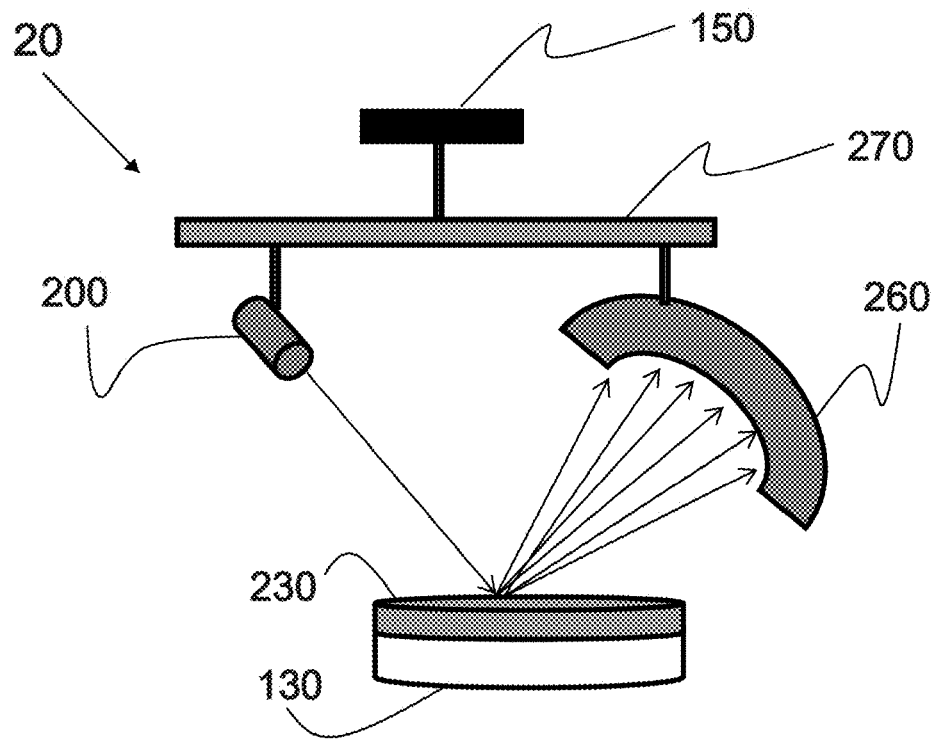
FIG. 8 presents a schematic illustration of a setup for measuring light scattering according to one embodiment of the invention.

Reference is now made to FIG. 8, which presents a schematic illustration of an embodiment 20 of a setup for making scattering measurements. A monochromatic light source 200 (e.g. a diode laser) produces output light at a predetermined wavelength in the visible/NIR range. The detector 260 in this embodiment comprises an array of detectors arranged in a semicircle, at a fixed distance within the chamber. The laser and detectors ring holder 270 may have the possibility to move horizontally by use of x-y scanning means 150 that will enable scanning most of the surface of the sample. The detectors will send the data to analyzing software which is used to create a scattering plot. The scattering plot will give additional data enabling determination of such physical characteristics as the roughness of the cell wall.

Figure 9:
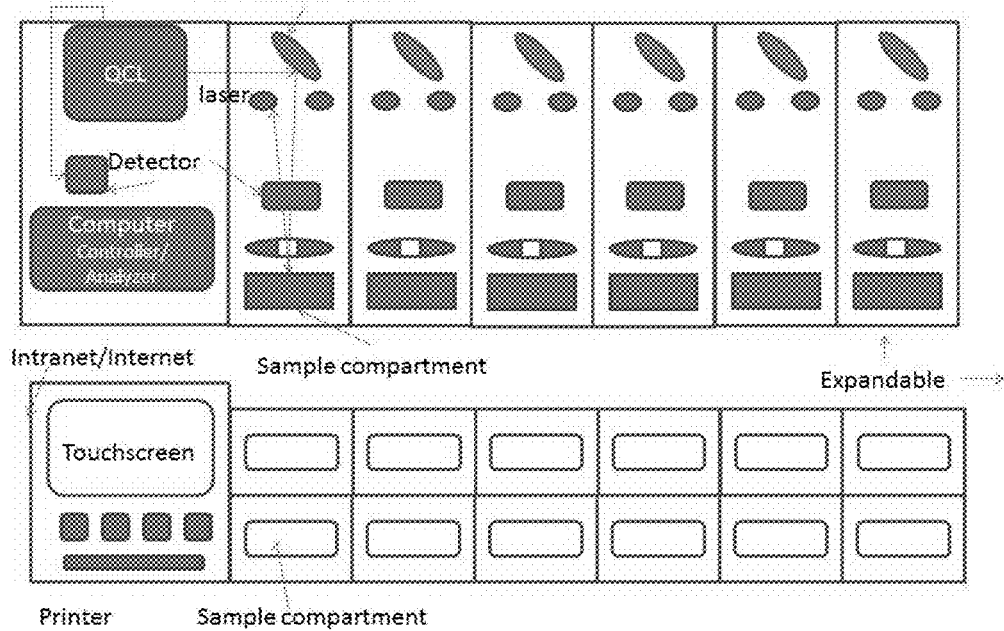
FIG. 9 presents a schematic illustration of a multiple compartment analyzer according to one embodiment of the invention.

In some embodiments of the invention, multiple samples are analyzed in a single batch. In these embodiments, sample compartment 220 comprises a multiple sample analyzer. Reference is now made to FIG. 9, which presents schematically one embodiment of such a multiple sample analyzer. The multiple sample analyzer comprises a plurality of sample compartments, into each of which a single sample is placed. In preferred embodiments of the invention, light source 200 is a tunable laser such as a quantum cascade laser. In the most preferred embodiments of the invention, the light source is tunable over a wavelength range of 8-12 micrometers. The spectral region of interest is measured by scanning the light source over the desired wavelength range. Light from the source is directed through an entrance aperture to a controllable flip mirror that directs the beam to the sample. If the flip mirror is moved to its other position, the light passes through a second aperture into the next sample compartment. The laser beam, which is directional and collimated, enables much smaller converging mirror than the FTIR source shown in FIG. 5 above. In the multiple compartment analyzer, the beam is expanded to cover the entire area of the optical cell mirror area; since the light output is collimated, the individual compartment is smaller than in the FTIR case. In preferred embodiments of the invention, a multiple pass cell is used. After interacting with the sample, the light is directed to the detector. The signal reaching the detector as a function of output wavelength of the light source is recorded and stored, and a spectrum built up from the measurements at each wavelength.

EXAMPLES

The following non-limiting examples are provided to illustrate various embodiments of the invention and to enable one of ordinary skill in the art to make use of it.

Example 1

Figure 10A:
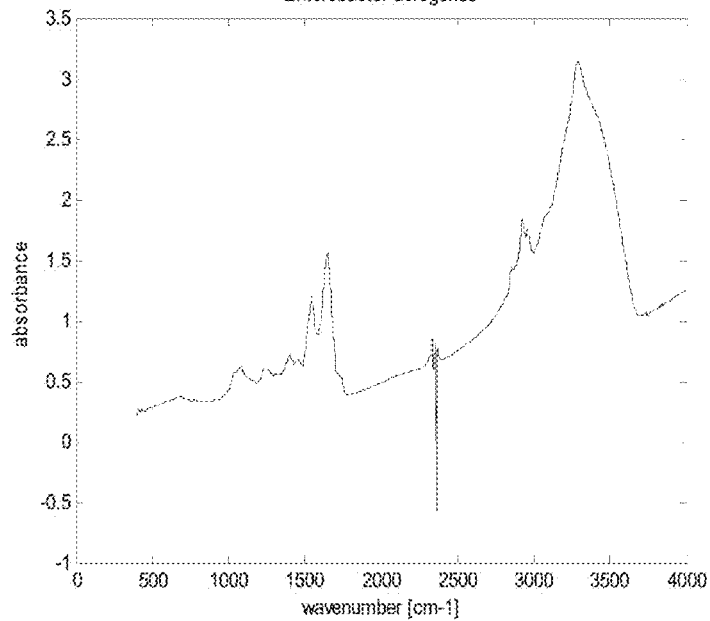
FIG. 10 presents infrared absorption spectra of two different species of bacteria.
Figure 10B:
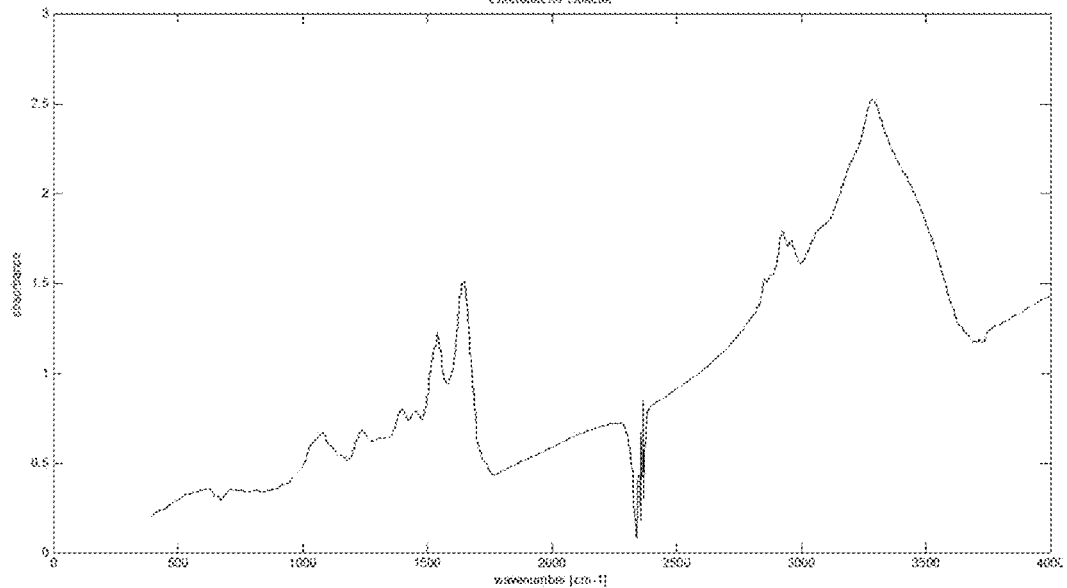
Figure 11:
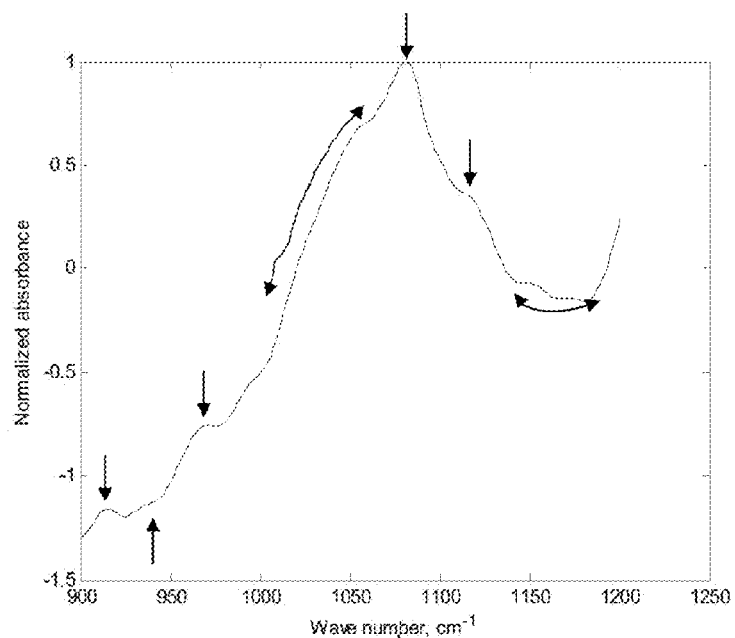
FIGS. 11-22 present additional infrared absorption spectra of various species of bacteria determined according to an embodiment of the invention disclosed herein; and, FIG. 23 presents graphs of results in PCA space illustrating the ability of the method disclosed herein to differentiate between different species of bacteria.
Figure 12A:
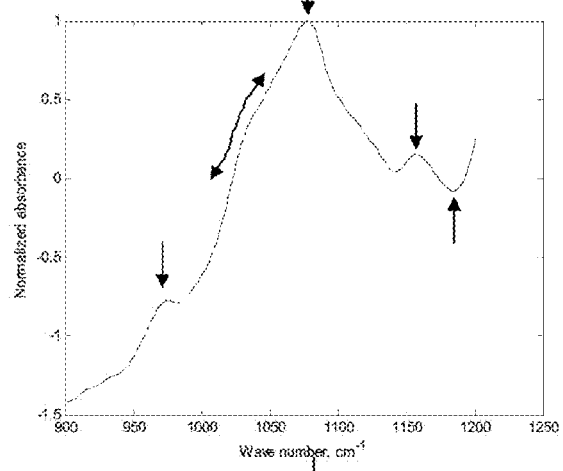
Figure 12B:
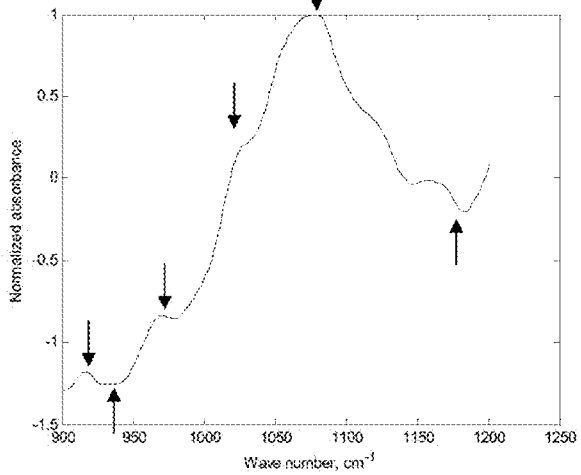
Figure 13A:
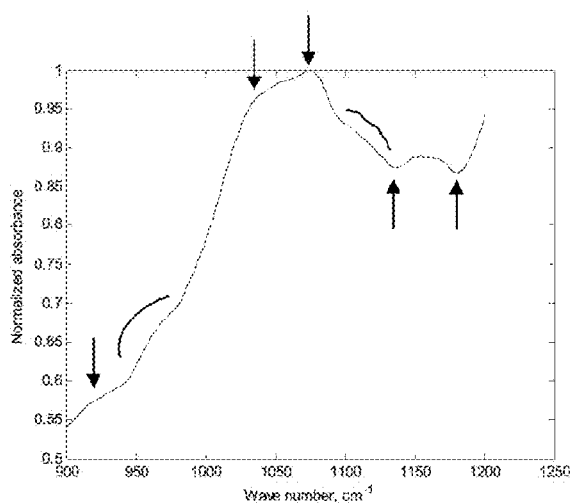
Figure 13B:
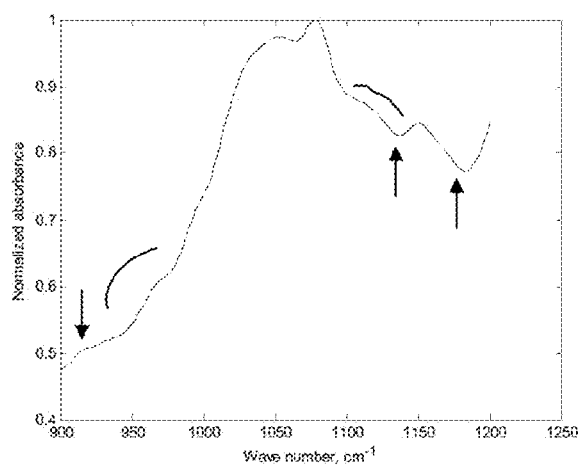
Figure 13C:
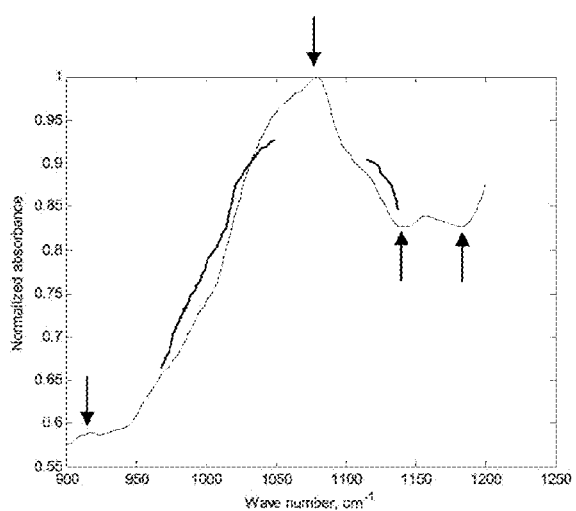
Figure 14A:
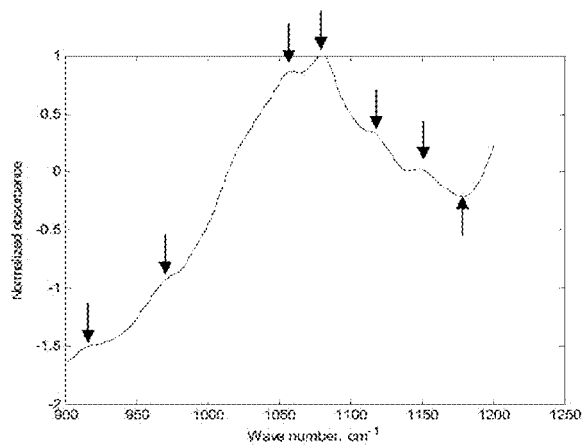
Figure 14B:
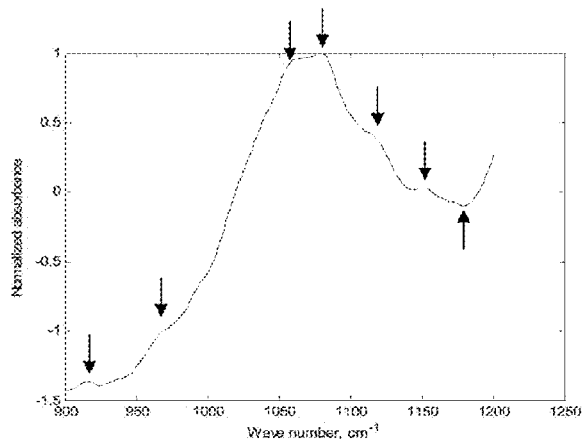
Figure 15:
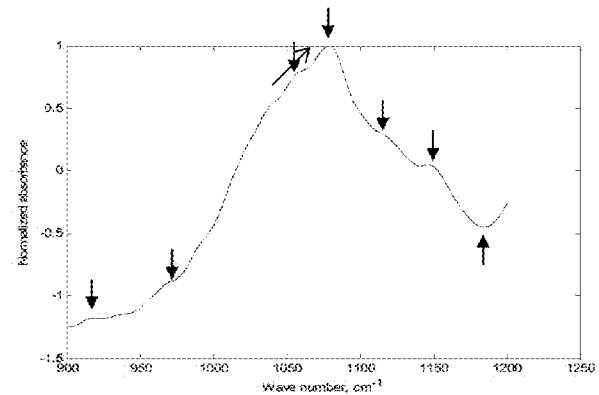
Figure 16A:
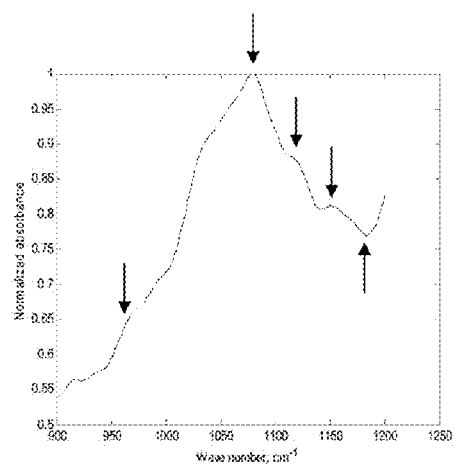
Figure 16B:
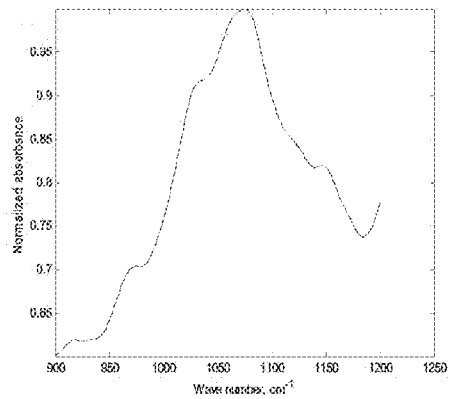
Figure 16C:
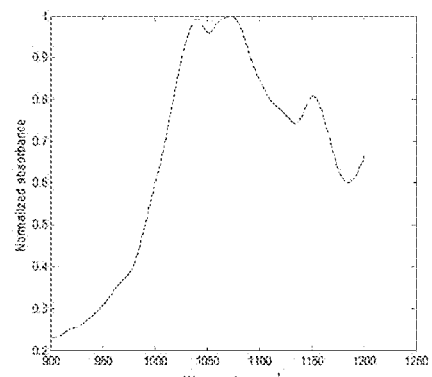
Figure 16D:
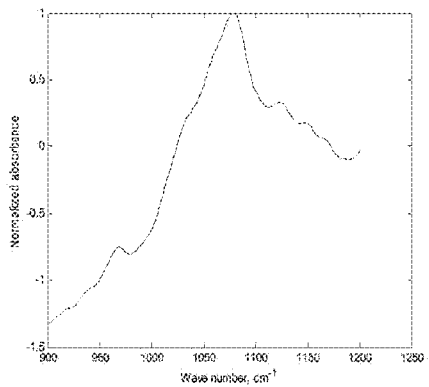
Figure 16E:
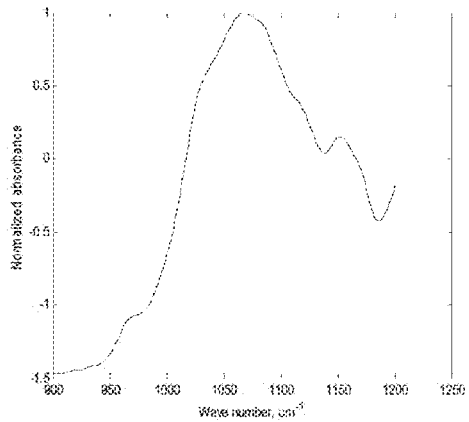
Figure 16F:
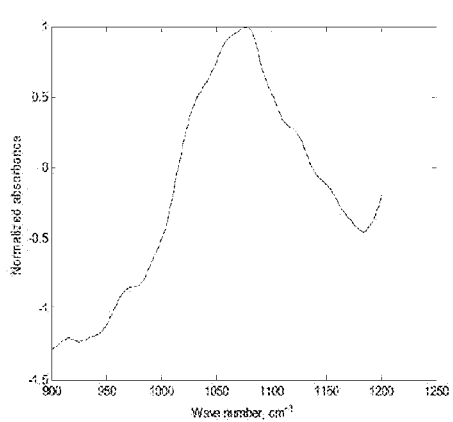
Figure 17:
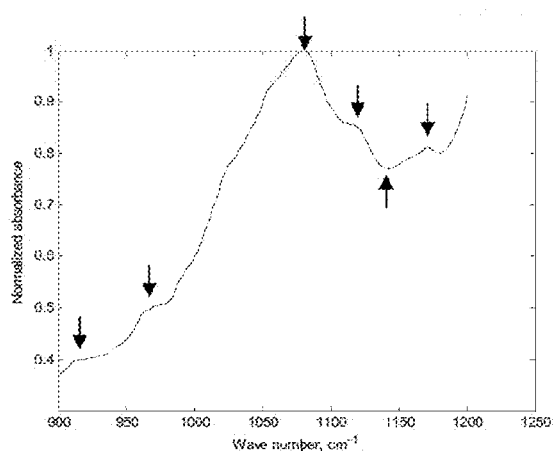
Figure 18A:
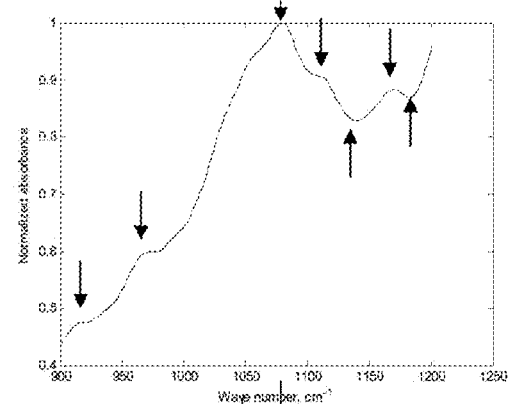
Figure 18B:
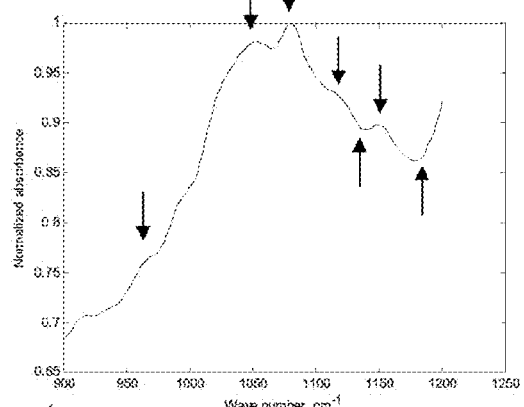
Figure 18C:
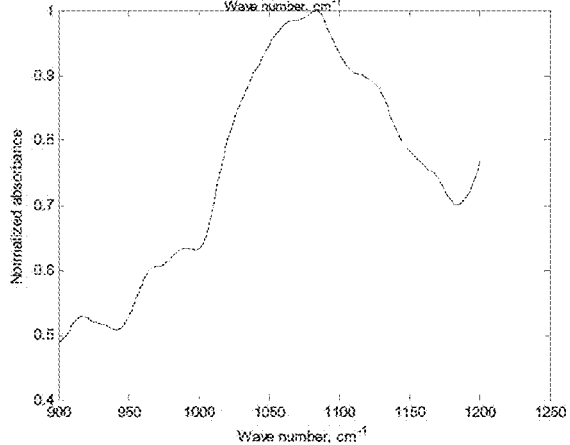
Figure 19A:
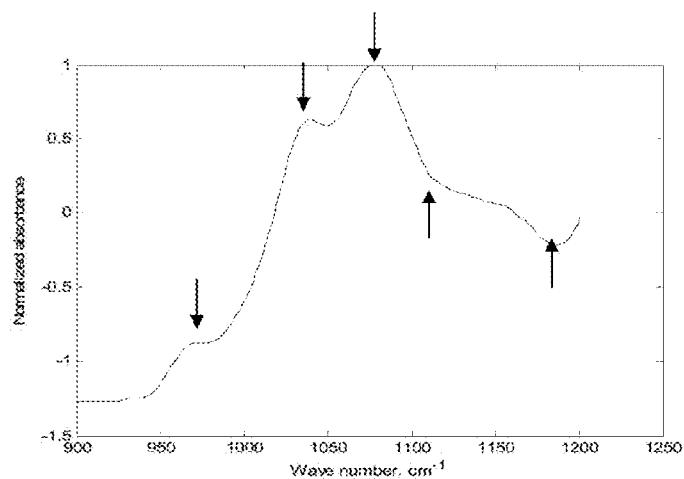
Figure 19B:
Figure 19C:
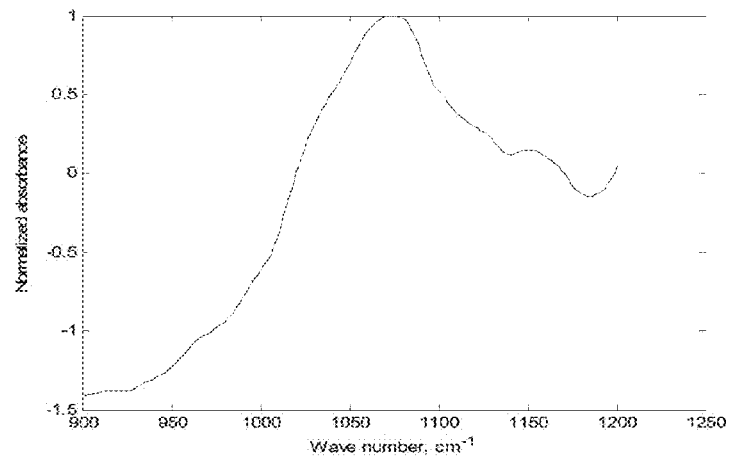
Figure 20:
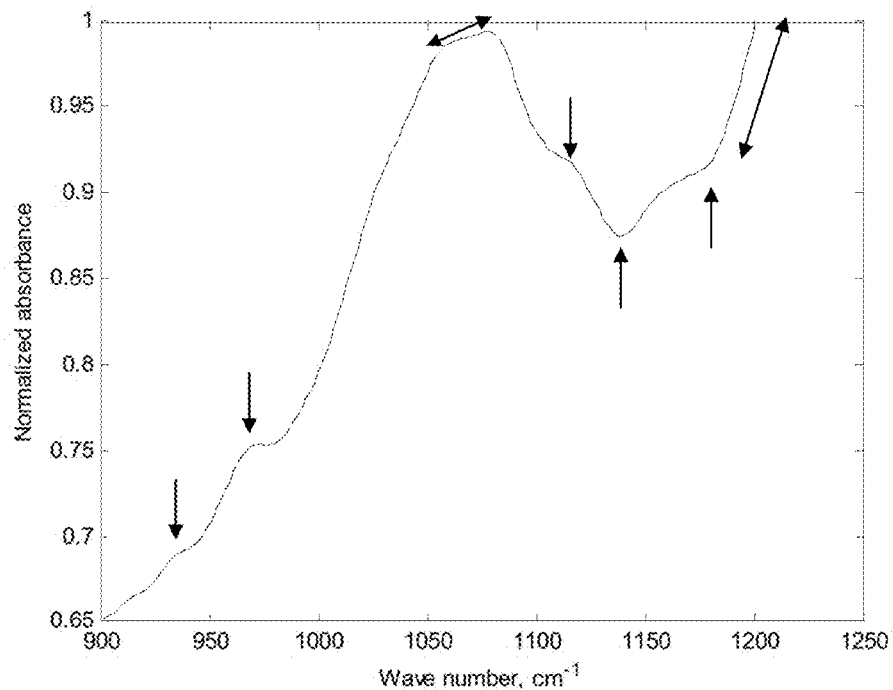
Figure 21:
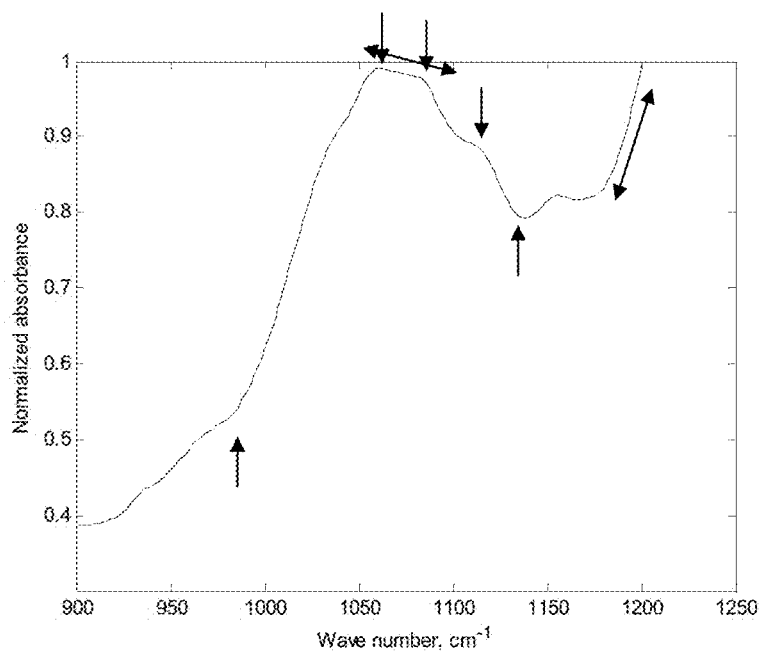
Figure 22:
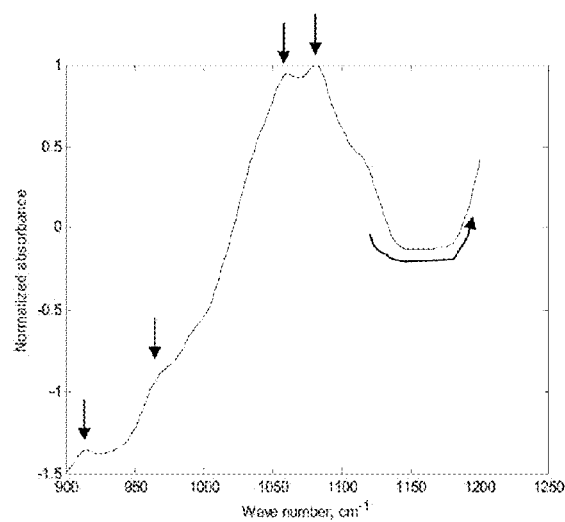

Each type of bacterium has a unique spectral signature. Although many types of bacteria have similar spectral signatures, there are still some spectral differences that are due to different proteins on the cell membrane and differences in the DNA/ RNA structure. Reference is now made to FIG. 10, which presents typical IR spectra (normalized absorbance as a function of energy in $cm^{-1}$) of two different species of bacteria, *Enterobacter aerogenes* (FIG. 10A) and *Enterobacter cloacae* (FIG. 10B). As can be seen from the figures, while the two spectra are broadly similar in structure, differences in detail can be seen, and these differences are sufficiently large to enable differentiation between the two species by use of the method disclosed herein.

Example 2

Reference is made to FIGS. 11-22, which provide additional examples of IR absorption spectra (normalized absorbance as a function of energy in cm$^{-1}$) of various species of bacteria are shown. In some cases, unique features of the spectrum are indicated by arrows. The species of bacteria, and number of strains of each species uniquely identified by the spectra, are summarized in Table 1. As can be seen from the figures, the method disclosed herein is able not only to distinguish between different species of bacteria, but between different strains of a single species of bacteria.

TABLE 1

| FIG. | Species of bacterium | number of strains |
|---|---|---|
| 11 | E. coli | 1 |
| 12 | Enterobacter aerogenes | 2 |
| 13 | Enterobacter cloacae | 3 |
| 14 | Enterococcus faecalis | 2 |
| 15 | Enterococcus faecium | 1 |
| 16 | Klebsellia pneumoniae | 6 |
| 17 | Proteus mirabilis | 1 |
| 18 | Pseud. aeruginosa | 3 |
| 19 | Serratia marcescens | 3 | teria pattern to each one of the models saved in memory during the training phase. A likelihood score was assigned to each model. The model that provided the maximum score was the selected as the classification decision.

Figure 23A:
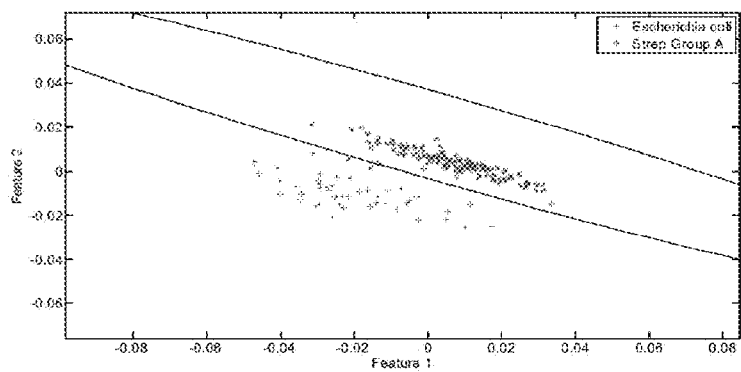
Figure 23B:
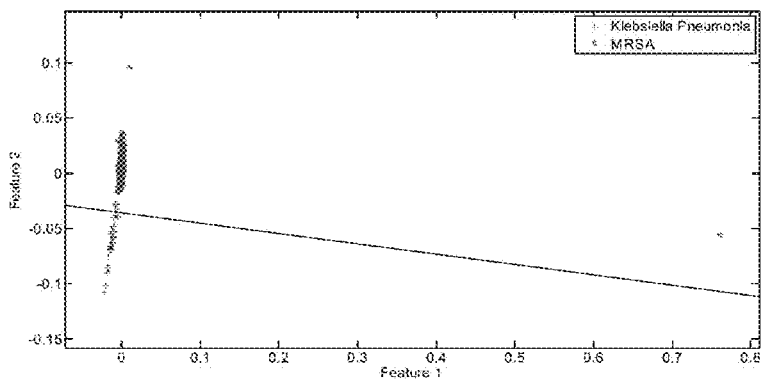

Reference is now made to FIG. 23, which presents two examples of identification of bacteria according to the method disclosed herein. Presented are graphs in PCA feature space. FIG. 23A shows a graph giving results for *E. coli* and *Strep* group A, and FIG. 23B shows a graph giving results for *Klebsellia pneumonia* and MRSA. In both cases, the differentiation between the two types of bacteria tested is clear.

Example 4

The method disclosed herein was used to identify 10 types of bacteria. In all cases, a minimum of 10 measurements were made. Table 2 shows a confusion matrix for the ten types of bacteria tested; the number of measurements mad is shown in parentheses.

TABLE 2

| | True | | | | | | | | | |
|---|---|---|---|---|---|---|---|---|---|---|
| Recog. | Acin. baumannii | E-coli | Enter. cloacae | Enter. Faecalis | Enter. Faecium | Prot. mirabilis | Pseud. Aerugino | Staph Epidermidis | Staph Aurcus | Strep Payogenes |
| Acin. baumannii | 73.9% (17) | 3.2 | 21.1 | 0 | 12.9 | 0 | 0 | 0 | 0 | 0 |
| E-coli | 0 | 80.6% (25) | 0 | 0 | 0 | 3.8 | 0 | 0 | 0 | 1 |
| Enter. cloacae | 17.4 | 3.2 | 63.2% (12) | 0 | 0 | 0 | 0 | 0 | 0 | 0 |
| Enter. Faecalis | 0 | 3.2 | 0 | 100% (30) | 3.2 | 0 | 3.7 | 0 | 0 | 0 |
| Enter. Faecium | 8.7 | 0 | 0 | 0 | 83.9% (26) | 0 | 0 | 0 | 0 | 0 |
| Prot. mirabilis | 0 | 3.2 | 0.0 | 0 | 0 | 46.2% (12) | 18.5 | 0 | 0 | 0 |
| Pseud. Aerugino | 0 | 3.2 | 15.8 | 0 | 0 | 46.2 | 78.8% (42) | 0 | 0 | 0 |
| Staph Epidermidis | 0 | 0 | 0 | 0 | 0 | 0 | 0 | 68.2% (15) | 0 | |
| Staph Aurcus | 4.3 | 3.2 | 0 | 0 | 0 | 3.8 | 3.8 | 0 | 100% (47) | 0 |
| Strep Payogenes | 0 | 0 | 0 | 0 | 0 | 0 | 0 | 31.8 | 0 | 96.0% (95) |

TABLE 1-continued

| FIG. | Species of bacterium | number of strains |
|---|---|---|
| 20 | Staph. aureus | 1 |
| 21 | Staph. epidermidis | 1 |
| 22 | Str. agalactiae gr. B | 1 |

Example 3

The following examples illustrate in-vitro examples to provide a method to distinguish between different kinds of bacteria.

First, during the training phase, the system was introduced with samples of each bacterium in the database, based on which a statistical model was estimated for each bacterium and saved in memory. This process resulted in several statistical models, each represents a type of bacteria. During the testing phase, the system was presented with "new" samples, i.e., samples that it never "saw" before, and data analysis and processing was performed. The system compared each bac- The system yielded an average correct classification rate of 84.1% (average error rate of 15.9%). The classification rates were lower for classes with fewer signatures in the database (e.g. *Enterobayct. cloacae* and *Prot. mirabilis*). The relatively small number of signatures in these cases led to less effective training during the training phase of the method. The overall success of the method in cases in which a sufficient number of measurements had been performed to enable effective training, demonstrating that the method disclosed herein is able to differentiate the various types of bacteria investigated. As the database of available bacteria and spectra increases in size, the method will provide even more accurate results.

We claim:

1. A method for spectroscopic detection and identification of microorganisms in culture, wherein said method comprises:
    obtaining at least one biological sample suspected of containing said microorganisms;
    culturing said biological sample, thereby producing a cultured sample;
    transferring said cultured sample to a sample cell;

interacting said sample with light obtained from a light source;

measuring at least a portion of said light remaining after said step of interacting;

constructing at least one data set from light measured in said step of measuring, wherein said data set comprises at least one type of data set selected from the group consisting of absorption spectrum, reflectance spectrum, fluorescence spectrum, scattering pattern, and interference pattern;

if said data set is a spectrum:

preprocessing said data set by performing at least one step selected from the group consisting of (a) correcting said data set for signals due to the presence of water in said cultured sample, (b) removing a baseline, (c) reducing noise, and (d) extracting a spectral region of interest, thereby producing a corrected data set;

extracting spectral features of interest from said corrected data set by using a method chosen from principal component analysis (PCA) and linear predictive coding, thereby producing a set of extracted spectral features;

classifying said extracted spectral features by using a method that incorporates a learning algorithm, thereby determining whether or not said microorganisms are present in said cultured sample; and, finding an optimal set of features by using a feature selection method;

if said data set is an interference pattern:

estimating a cell wall thickness of said microorganisms from said interference pattern; and, classifying said cell wall thickness, thereby determining whether or not said microorganisms are present in said cultured sample;

if said data set is a scattering pattern:

estimating a cell wall roughness of said microorganisms from said scattering pattern; and, classifying said cell wall roughness, thereby determining whether or not said bacteria are present in said cultured sample.

2. The method according to claim 1, wherein said biological sample is selected from the group consisting of sneeze, saliva, mucus, bile, urine, vaginal secretions, middle ear aspirate, pus, pleural effusions, synovial fluid, abscesses, cavity swabs, serum, blood and spinal fluid.

3. The method according to claim 1, wherein said step of smearing comprises smearing on the reflective surface of a mirror.

4. The method according to claim 1, wherein said step of culturing is followed by a step of choosing a plurality of colonies.

5. The method according to claim 1, wherein said step of transferring said cultured sample to a sample cell comprises transferring said cultured sample to a multiple pass cell.

6. The method according to claim 1, wherein said step of obtaining at least one cultured sample comprises obtaining a plurality of cultured samples; said step of transferring said cultured sample to a sample cell comprises transferring each of said plurality of cultured samples to a sample cell disposed within a separate compartment of a multiple compartment analyzer; and said step of constructing a data set comprises constructing separately a data set for each of said plurality of samples.

7. The method according to claim 1, wherein at least one of the following is true:

said step of interacting comprises interacting said sample with light obtained from a light source selected from a light source of an FTIR spectrometer and a laser, and said step of constructing a data set comprises constructing a spectrum selected from the group consisting of infrared absorption spectrum and infrared reflectance spectrum;

said step of interacting comprises interacting said sample with light obtained from a light source selected from the group consisting of a light source of a Raman spectrometer and a laser, and said step of constructing a data set comprises constructing a Raman spectrum; and, said step of interacting comprises interacting said sample with light obtained from a light source that emits light in a wavelength range selected from the group consisting of UV and visible light, and said step of constructing a data set comprises constructing a spectrum selected from the group consisting of UV-VIS absorption spectrum and UV-VIS reflectance spectrum.

8. The method according to claim 7, wherein said step of constructing a data set comprises constructing an infrared absorption spectrum, and said step of preprocessing comprises extracting a spectral range selected from the group consisting of about 850-1000 $cm^{-1}$; about 990-1190 $cm^{-1}$; about 1180-1290 $cm^{-1}$; about 1235-1363 $cm^{-1}$; about 1300-1350 $cm^{-1}$; about 1500-1800 $cm^{-1}$; about 1550-1650 $cm^{-1}$; about 1720-1780 $cm^{-1}$; about 2800-3050 $cm^{-1}$; about 2836-2995 $cm^{-1}$; and about 3000-3300 $cm^{-1}$.

9. The method according to claim 1, wherein said step of correcting said data set for the presence of data due to the presence of water in said cultured sample comprises a step chosen from the group consisting of (a) performing simple filtering by subtracting from said data set a data set constructed from an average of other data sets; (b) subtracting a reference data set from said data set; and (c) performing adaptive filtering by adaptive filtering using a reference signal to produce an optimal reduction in the contribution of the water signal to the as-measured sample spectrum.

10. The method according to claim 1, wherein at least one of the following is true:

said step of preprocessing said data comprises reducing noise by using at least one technique selected from the group consisting of linear filtering, adaptive filtering, using a Savitzky-Golay filter, low pass filtering, and spectral subtraction.

said step of using a PCA method comprises:

obtaining first and second derivatives of said data set; and, obtaining two coefficients for each derivative obtained;

said set of extracted spectral features comprises spectral features selected from the group consisting of peak correlation, peak wavelength, peak height, peak width, peak cross section, peak area, at least one of the coefficients of a fitted polynomial curve, the total sum of areas under at least two peaks of the signal, linear predictive coding (LPC), mean value of the signal, variance value of the signal, skewness value, kurtosis value, Gaussian set of parameters $(\mu, \sigma, A_i)$ peak intensity ratios, wavelet coefficients, and derivatives thereof;

said feature selection method is selected from the group consisting of sequential feature selection and genetic algorithm; and, said learning algorithm is selected from the group consisting of Bayes classifier, support vector machine (SVM), linear discriminant functions, Fisher's linear discriminant, C4.5 algorithm tree, K-nearest neighbor, weighted K-nearest neighbor, Hierarchical clustering algorithm, a learning algorithm that incorporates an ensemble classifier that uses the methods developed by Breiman and Cutler, hidden Markov model, Gaussian mixture model (GMM), K-mean clustering algorithm, Ward's clustering algorithm, minimum least squares, and neural network algorithms.

11. The method according to claim 10, wherein said learning algorithm incorporates an ensemble classifier that uses the methods developed by Breiman and Cutler.

12. The method according to claim 1, wherein said step of classifying is performed based on parameters of a fit obtained by said learning algorithm based on features that have a minimum significance threshold.

13. The method according to claim 1, wherein said microorganisms comprise microorganisms selected from the group consisting of yeast and fungi.

14. The method according to claim 1 wherein:
said microorganisms comprise antibiotic-resistant and antibiotic-sensitive strains of a single species of bacterium;
said at least one data set comprises a spectrum, an interference pattern, and a scattering pattern; and,
said method comprises:
determining at least one chemical characteristic of bacteria within said sample from said spectrum;
estimating a cell wall thickness of bacteria within said sample from said interference pattern;
estimating a cell wall roughness of bacteria within said sample from said scattering pattern; and,
said step of classifying comprises classifying results of all of said spectrum, said interference pattern, and said scattering pattern.

15. An apparatus for spectroscopic detection and identification of bacteria in culture, wherein said apparatus comprises:
a light source;
a sample compartment comprising:
a multiple compartment analyzer comprising a plurality of compartments, each compartment of said multiple compartment analyzer comprising:
an entrance aperture;
an exit aperture aligned with said entrance aperture;
a cell;
multiple pass sample cell holding means for holding a sample cell containing a sample suspected of containing said bacteria, said sample compartment in optical connection with said light source; and,
a switching device capable of directing light entering said compartment through said entrance aperture either to said cell or to said exit aperture without entering said cell;
a detector for measuring light following interaction between light emitted by said light source and said sample;
control means in electronic connection with said light source and said detector for controlling collection of data; and,
analyzing means for performing preprocessing of said data, analysis of said data, and classification of said data;
wherein said multiple pass cell comprises:
a parabolic mirror;
light converging means for converging output of said light source and disposed such that said output of said light source impinges on said parabolic mirror;
light coupling means for directing light from multiple pass cell to a detector;
a stage comprising sample holding means for holding a sample, said stage disposed such that at least a portion of light passing from said light source to said parabolic mirror via said light converging means and then reflected from said parabolic mirror will impinge upon a sample attached to said stage via said sample holding means and such that light reflected onto said parabolic mirror from said sample will be directed to a location other than said sample; and,
a plurality of n folding mirrors disposed such that:
light reflected from said sample to said parabolic mirror will impinge on one of said folding mirrors;
for m=1 to n−1, light impinging on an mth folding mirror will be reflected back to said parabolic mirror such that it will then be reflected onto said sample, and such that light reflected from said sample will be reflected from said parabolic mirror to an (m+1)th folding mirror; and,
for m=n, light reflected from said mth folding mirror will be directed to said light coupling means.

16. The apparatus according to claim 15, wherein said switching device is selected from the group consisting of:
a movable flip mirror movable between a first position in which light entering said compartment through said entrance aperture is reflected from said mirror into said cell and a second position in which light entering said compartment through said entrance aperture passes to said exit aperture without entering said cell; and,
an optical switch.

17. The apparatus according to claim 15, wherein said plurality of n folding mirrors are disposed in pairs around the circumference of a circle.

18. The apparatus according to claim 15, wherein said light source emits light in a wavelength range selected from the group consisting of UV, visible, IR, near-IR, mid-IR, far-IR, microwave, and terahertz.

19. The apparatus according to claim 15, wherein said light source comprises a light source selected from the group consisting of a light source of an FTIR spectrometer; a light source of a Raman spectrometer; and a laser.

* * * * *